US009737450B2

(12) United States Patent
Peterson et al.

(10) Patent No.: US 9,737,450 B2
(45) Date of Patent: Aug. 22, 2017

(54) HYPEROXIC THERAPY SYSTEMS, METHODS AND APPARATUS

(71) Applicant: MICROBARIC OXYGEN SYSTEMS, LLC, Longboat Key, FL (US)

(72) Inventors: Russell E. Peterson, Longboat Key, FL (US); Michael W. Allen, Furlong, PA (US); Glenn Butler, Tarrytown, NY (US)

(73) Assignee: MICROBARIC OXYYGEN SYSTEMS, LLC, Longboat Key, FL (US)

( * ) Notice: Subject to any disclaimer, the term of this patent is extended or adjusted under 35 U.S.C. 154(b) by 489 days.

(21) Appl. No.: 14/476,717

(22) Filed: Sep. 3, 2014

(65) Prior Publication Data

US 2015/0059738 A1    Mar. 5, 2015

Related U.S. Application Data

(60) Provisional application No. 61/873,811, filed on Sep. 4, 2013, provisional application No. 61/873,817, filed on Sep. 4, 2013.

(51) Int. Cl.
*A61B 5/08*    (2006.01)
*A61M 16/00*    (2006.01)
(Continued)

(52) U.S. Cl.
CPC ............... *A61G 10/04* (2013.01); *A61B 5/08* (2013.01); *A61K 33/40* (2013.01);
(Continued)

(58) Field of Classification Search
CPC .............. A61M 16/00; A61M 16/0627; A61M 16/0672; A61M 16/0677; A61M 16/10;
(Continued)

(56) References Cited

U.S. PATENT DOCUMENTS 2,649,583 A    8/1953    Schaeffer
3,400,712 A    9/1968    Finan
(Continued)

FOREIGN PATENT DOCUMENTS

| EP | 2376168 B1 | 11/2013 |
| IT | 1266185 B1 | 12/1996 |
| WO | WO 02/39558 A2 | 5/2002 |

OTHER PUBLICATIONS

Rossignol et al., "The effects of hyperbaric oxygen therapy on oxidative stress, inflammation, and symptoms in children with autism: an open-label pilot study," BMC Pediatrics—BioMed Central—Nov. 16, 2007, pp. 1-13.
(Continued)

*Primary Examiner* — Annette Dixon
(74) *Attorney, Agent, or Firm* — BCF LLP

(57) ABSTRACT

The present invention provides systems, methods, and apparatus for applying a hyperoxic therapy delivery system to a patient; administering hyperoxic gas to the patient according to an oxygen dose-response model; and adjusting the administration of the hyperoxic gas to the patient based upon monitored parameters related to a condition of the patient. Numerous additional features are disclosed.

21 Claims, 10 Drawing Sheets

(51) Int. Cl.
*A61G 10/04* (2006.01)
*A61K 33/40* (2006.01)
*A61M 16/06* (2006.01)
*A61M 16/10* (2006.01)
*A61M 16/20* (2006.01)
*A61G 10/02* (2006.01)

(52) U.S. Cl.
CPC ....... *A61M 16/0627* (2014.02); *A61G 10/026* (2013.01); *A61M 16/101* (2014.02); *A61M 16/1065* (2014.02); *A61M 16/209* (2014.02); *A61M 2202/0208* (2013.01); *A61M 2205/18* (2013.01); *A61M 2205/3358* (2013.01)

(58) Field of Classification Search
CPC .. A61M 16/12; A61M 16/202; A61M 16/204; A61M 2016/0015; A61M 2016/0021; A61M 2016/0024; A61M 2016/0027; A61M 2016/0039; A61M 2016/1025; A61M 2202/0208; A61M 2202/03; A61M 2205/14; A61M 2205/18; A61M 2205/3375; A61M 2205/3553; A61M 2205/3584; A61M 2205/52; A61M 2205/581; A61M 2205/583; A61M 2205/70; A61M 2205/8206; A61M 2205/8212; A61M 2230/005; A61M 2230/205; A61M 2230/435; A61M 2230/63
USPC ............ 128/202.22, 204.18, 204.21, 204.22, 128/204.23, 204.26, 205.22, 205.24, 128/207.14, 207.18
See application file for complete search history.

(56) References Cited

U.S. PATENT DOCUMENTS

| | | | |
|---|---|---|---|
| 3,439,966 A | 4/1969 | Perkins | |
| 3,577,977 A | 5/1971 | Ritzinger et al. | |
| 3,744,055 A | 7/1973 | Brendgord | |
| 3,762,407 A | 10/1973 | Shonerd | |
| 3,802,427 A | 4/1974 | Banjavich | |
| 3,877,427 A | 4/1975 | Alexeev et al. | |
| 3,889,670 A | 6/1975 | Loveland et al. | |
| 3,957,043 A | 5/1976 | Shelby | |
| 4,034,416 A | 7/1977 | Buffkin | |
| 4,116,237 A | 9/1978 | Birch | |
| 4,186,735 A | 2/1980 | Henneman et al. | |
| 4,454,878 A | 6/1984 | Morrison | |
| 4,458,680 A | 7/1984 | Childers | |
| 4,620,538 A | 11/1986 | Koegel | |
| 4,633,859 A | 1/1987 | Reneau | |
| 4,706,664 A * | 11/1987 | Snook | A61M 16/00 128/204.23 |
| 5,044,017 A | 9/1991 | Kirby | |
| 5,060,644 A | 10/1991 | Loori | |
| 5,090,972 A | 2/1992 | Eller | |
| 5,109,832 A | 5/1992 | Proctor et al. | |
| 5,109,837 A | 5/1992 | Gamow | |
| 5,335,653 A | 8/1994 | Blomqvist et al. | |
| 5,526,818 A | 6/1996 | Ruismaki | |
| 5,558,086 A * | 9/1996 | Smith | A61M 16/00 128/204.23 |
| 5,582,574 A | 12/1996 | Cramer | |
| 5,603,315 A * | 2/1997 | Sasso, Jr. | A61M 16/00 128/202.22 |
| 5,660,171 A | 8/1997 | Kim et al. | |
| 5,682,877 A * | 11/1997 | Mondry | A61M 16/10 128/204.22 |
| 5,685,293 A | 11/1997 | Watt | |
| 5,697,364 A * | 12/1997 | Chua | A61M 16/00 128/204.18 |
| 5,819,728 A | 10/1998 | Ritchie | |
| 5,865,722 A | 2/1999 | Heng | |
| 6,062,215 A | 5/2000 | Leininger et al. | |
| 6,347,630 B1 | 2/2002 | Takahashi et al. | |
| 6,484,716 B1 | 11/2002 | Leininger et al. | |
| 6,497,231 B1 | 12/2002 | White | |
| 6,701,920 B1 | 3/2004 | Cox | |
| 6,792,623 B2 | 9/2004 | Luppi | |
| 6,796,307 B1 | 9/2004 | Hughson et al. | |
| 6,814,076 B2 | 11/2004 | Shusterman et al. | |
| 6,854,459 B1 | 2/2005 | Cox | |
| 7,198,045 B2 | 4/2007 | Risley et al. | |
| 7,520,277 B1 | 4/2009 | Grady | |
| 7,540,283 B2 | 6/2009 | Loori et al. | |
| 7,556,040 B2 | 7/2009 | Meyer et al. | |
| 8,336,113 B2 | 12/2012 | Uttrachi | |
| 8,464,716 B2 | 6/2013 | Kuehne et al. | |
| 8,535,064 B2 | 9/2013 | Linton | |
| 8,621,672 B2 | 1/2014 | Chuback | |
| 2001/0047035 A1 | 11/2001 | Boykin, Jr. | |
| 2003/0159700 A1 | 8/2003 | Laufer et al. | |
| 2004/0261796 A1 | 12/2004 | Butler | |
| 2006/0137686 A1 | 6/2006 | Macris | |
| 2008/0190433 A1 | 8/2008 | Petyaev | |
| 2008/0210234 A1 | 9/2008 | O'Brien et al. | |
| 2009/0044800 A1 | 2/2009 | Jorn | |
| 2009/0143751 A1 | 6/2009 | Loori et al. | |
| 2009/0199855 A1 * | 8/2009 | Davenport | A61M 16/00 128/204.23 |
| 2010/0178347 A1 | 7/2010 | Bullock et al. | |
| 2010/0300444 A1 * | 12/2010 | Decker | A61M 16/00 128/204.23 |
| 2010/0316729 A1 | 12/2010 | Franks et al. | |
| 2010/0316733 A1 | 12/2010 | Locklear | |
| 2011/0226240 A1 | 9/2011 | Navalesi et al. | |
| 2011/0240017 A1 | 10/2011 | Butler et al. | |
| 2013/0042877 A1 | 2/2013 | Harvie | |

OTHER PUBLICATIONS

Rossignol et al., "Hyperbaric Treatment for Children With Autism: A Multicenter, Randomized, Double-Blind, Controlled Trial," BMC Pediatrics—BioMed Central—Mar. 13, 2009, pp. 1-15.
Chungpaibulpatana et al., "Hyperbaric Oxygen Therapy in Thai Autistic Children," J Med Assoc Thai, vol. 91 No. 8, 2008, pp. 1232-1238.
Marois et al., "Letter to the Editor—Hyperbaric oxygen therapy and cerebral palsy," Developmental Medicine & Child Neurology 2003, 45: pp. 646-648.
Montgomery et al., "Effects of hyperbaric oxygen therapy on children with spastic diplegic cerebral palsy: a pilot project," Undersea Hyperb Med. 1999 Winter; 26(4): pp. 235-242.
Office Action in related U.S. Appl. No. 13/078,776 dated Aug. 13, 2013.
Dec. 13, 2013 Reply to Aug. 13, 2013 Office Action in related U.S. Appl. No. 13/078,776.
Amendment submitted with RCE in related U.S. Appl. No. 13/078,776, filed Sep. 25, 2014.
Allen et al., U.S. Appl. No. 14/476,713, titled: "Hyperoxic Therapy Systems, Methods and Apparatus," filed Sep. 3, 2014.
Lascano et al., "Kidney Function Assessment by Creatine-Based Estimation Equations," www.clevelandclinicmeded.com/medicalpubs/diseasemanagement/nephrology/kidnet-function/.
Nordmark et al., "Comparison of the Gross Motor Function Measure and Pediatric Evaluation of Disability Inventory in assessing motor function in children undergoing selective dorsal rhizotomy" in Dev Med Child Neurol, 2000;42:245-252.
Weathers et al., The PTSD checklist: Reliability, validity, & diagnostic utility which was a paper presented at the Annual Meeting of the International Society for Traumatic Stress Studies, San Antonio, TX in 1993.
Lovell et al., "Measurement of Symptoms Following Sports-Related Concussion: Reliability and Normative Data for the Post-Concussion Scale," Appl. Neruopsychol, 2006;13:166-174.
Bennett et al., "UHMS Position Paper the Treatment of Autism Spectrum Disorder With Hyperbaric Oxygen Therapy," http://c.

(56) References Cited

OTHER PUBLICATIONS ymcdn.com/sites/membership.uhms.org/resource/resmgr/position_papers/autism_position_paper.pdf.
Final Office Action in related U.S. Appl. No. 13/078,776 dated Mar. 26, 2014.
Examiner Interview Summary in related U.S. Appl. No. 13/078,776 dated Dec. 20, 2013.
Rogers, NM et al., "Hyperbaric oxygen as effective adjuvant therapy in the treatment of distal calcific uraemic arteriolopathy," NDT Plus. 2008. pp. 1-6; pp. 1-2.
Wolf, G et al., "The Effect of Hyperbaric Oxygen on Symptoms after Mild Traumatic Brain Injury," Journal of Neurotrauma. vol. 29. Nov. 20, 2012. pp. 2606-2612; abstract.
Lacey, DJ et al., "Effects of Hyperbaric Oxygen on Motor Function in Children with Cerebral Palsy," Annals of Neurology, Oct. 2012, vol. 72, No. 5, pp. 695-703; p. 1, methods section.
International Search Report & Written Opinion of International Application No. PCT/US14/53960 mailed Nov. 18, 2014.
International Preliminary Report on Patentability, PCT/US2014/053959 (WO2015/034967), mailed Mar. 8, 2016.
International Preliminary Report on Patentability, PCT/US2014/053960 (WO2015/034968), mailed Mar. 8, 2016.
Office Action in copending U.S. Appl. No. 14/476,713, mailed Dec. 19, 2016.
Non-Final Office Action in related U.S. Appl. No. 13/078,776 dated Mar. 26, 2015.
International Search Report & Written Opinion of International Application No. PCT/US14/53959 mailed Feb. 24, 2015.

* cited by examiner

HYPEROXIC THERAPY SYSTEMS, METHODS AND APPARATUS

RELATED APPLICATIONS

This application claims priority to and the benefit of U.S. Patent Application Ser. No. 61/873,811 filed Sep. 4, 2013, and titled "HYPEROXIC THERAPY SYSTEMS, METHODS AND APPARATUS"; and U.S. Patent Application Ser. No. 61/873,817 filed Sep. 4, 2013, and titled "HYPEROXIC THERAPY SYSTEMS, METHODS AND APPARATUS", each of which is hereby incorporated by reference herein in its entirety for all purposes.

FIELD

The present invention generally relates to hyperoxic therapy, and more particularly is directed to systems, methods and apparatus for delivering hyperoxic therapy.

BACKGROUND

The hyperbaric medical establishment holds that hyperbaric oxygen therapy is not effective with "normal wounds" (i.e., wounds that will heal normally without special intervention). Despite this established position, several studies have produced confounding results that indicate hyperbaric oxygen therapy can produce both positive and negative outcomes for the healing of normal wounds in both soft tissue and bone. A detailed review of the prior art indicates that there is no clear explanation or understanding as to when, how, and under what conditions hyperbaric oxygen therapy can be beneficial in such cases. Thus, what is needed are systems, methods and apparatus that can consistently produce beneficial outcomes using hyperoxic therapy over the domain from normal pressure to hyperbaric pressure.

SUMMARY

The present invention provides systems, methods and apparatus for effective beneficial use of hyperoxic therapy for enhancing the healing of normal wounds such as cosmetic, oral, hair transplant, and the like surgery and for improving neurological conditions such as traumatic brain injury, cerebral palsy, autism spectrum disorders and the like, when applied in appropriate doses.

In some embodiments, the present invention provides systems, methods and apparatus for applying a hyperoxic therapy delivery system to a patient; administering hyperoxic gas to the patient according to an oxygen dose-response model; and adjusting the administration of the hyperoxic gas to the patient based upon monitored parameters related to a condition of the patient.

In some embodiments, the present invention provides a method. The method includes applying a hyperoxic therapy delivery system to a patient; administering hyperoxic gas to the patient according to an oxygen dose-response model; and adjusting the administration of the hyperoxic gas to the patient based upon monitored parameters related to a condition of the patient.

In other embodiments, the present invention provides an alternative method. The alternative method includes determining an initial oxygen dose-response model for a patient based upon the patient and a condition to be treated; applying an initial oxygen dose to the patient in an initial treatment session based upon the initial oxygen dose-response model; reassessing the patient's condition periodically; adjusting the oxygen dose-response model to reflect the patient's reassessed condition; and determining an adjusted oxygen dose based upon the adjusted oxygen dose-response model.

In yet other embodiments, the present invention provides a system. The system includes a processor; a memory coupled to the processor and operative to store instructions executable on the processor to determine an initial oxygen dose-response model for a patient based upon the patient and a condition to be treated; indicate an initial oxygen dose to apply to the patient in an initial treatment session based upon the initial oxygen dose-response model; receive data for reassessing the patient's condition periodically; adjust the oxygen dose-response model to reflect the patient's reassessed condition; and determine an adjusted oxygen dose based upon the adjusted oxygen dose-response model.

In still other embodiments, the present invention provides a breathing hood assembly. The breathing hood assembly includes an assembly including a hood ring and a sealable tent portion, wherein the hood ring includes a first portion and a second portion adapted to releasably attach to an O-ring finish of the sealable tent portion; and a neckseal ring assembly including an elastic neck dam and a neckseal ring, wherein the neckseal ring includes a first portion and a second portion adapted to releasably attach to an O-ring finish of the neck dam. The hood ring is adapted to sealably engage the neckseal ring.

In yet still other embodiments, the present invention provides an alternative breathing hood assembly. The alternative breathing hood assembly includes a tent assembly including a hood ring and a sealed tent portion; and a neckseal ring assembly including a torso seal assembly and a neckseal ring. The hood ring is adapted to sealably engage the neckseal ring.

In some other embodiments, the present invention provides a hyperoxic gas delivery system. The hyperoxic gas delivery system includes a breathing hood assembly; and a control unit coupled to the breathing hood assembly via an umbilical. The control unit is adapted to deliver hyperoxic gas to the breathing hood assembly via the umbilical at approximately one atmosphere.

Numerous other aspects are provided. Other features and aspects of the present invention will become more fully apparent from the following detailed description, the appended claims and the accompanying drawings.

DETAILED DESCRIPTION

Figure 1:
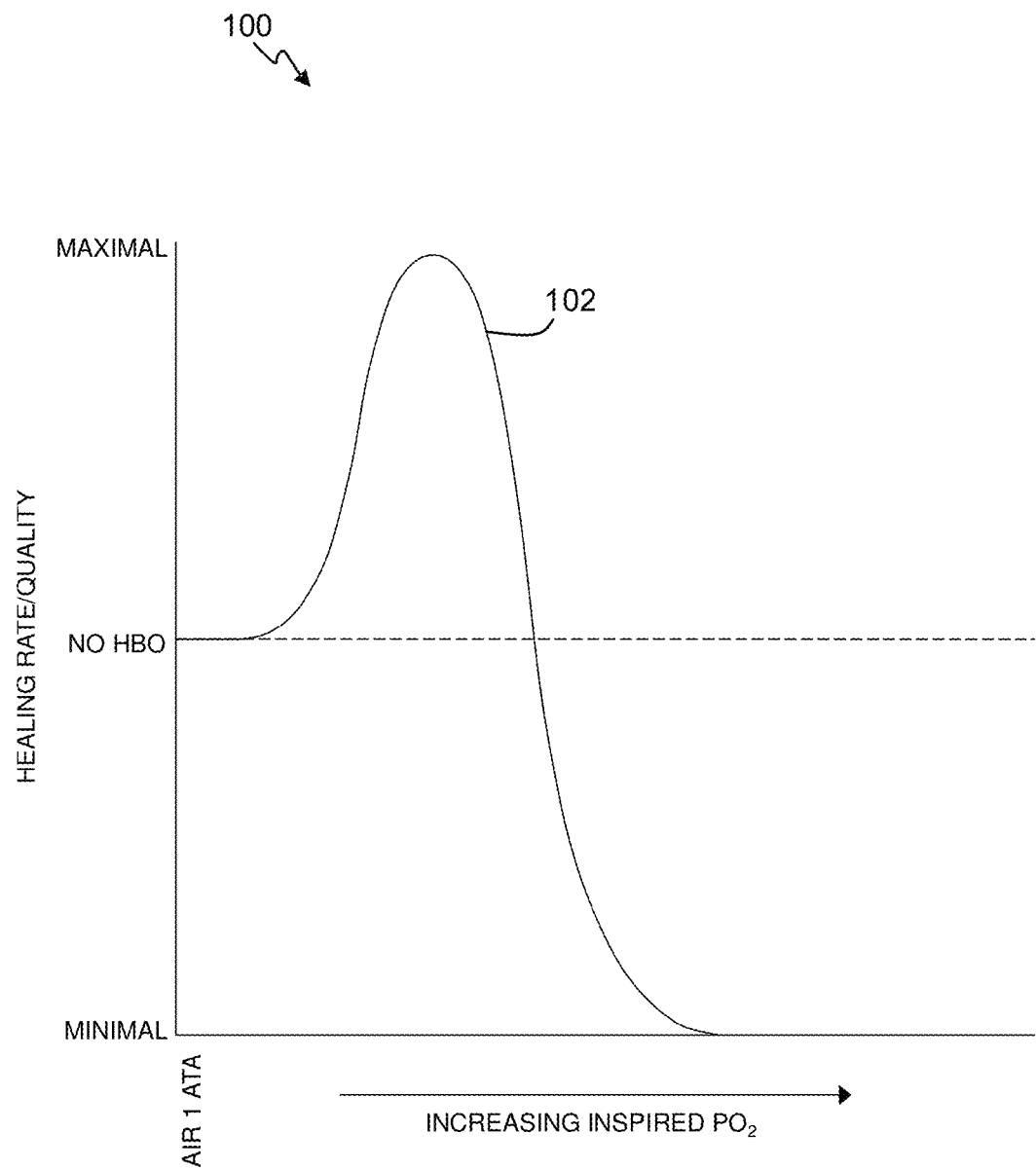
FIG. 1 is a graph of healing rate/quality versus oxygen treatment dosage according to some embodiments of the present invention.

Inventive systems, methods and apparatus are provided for effective beneficial use of a novel hyperoxic therapy for enhancing healing of normal wounds, providing prophylaxis against development of conditions such as repetitive strain injuries, and providing more beneficial outcomes in treating conditions such as cerebral palsy, autism spectrum disorders, brain trauma, glomerulonephritis, and other conditions when applied in appropriate doses. The inventors of the present invention have determined that use of an oxygen dose-response methodology of administering and adjusting hyperoxic therapy provides such efficacy. In other words, by treating patients based upon a hyperoxic dosage dictated by a model that defines changing efficacious doses over time, beneficial results can be consistently obtained. As used herein, the term "normal wounds" refers to wounds that would otherwise heal without exceptional medical intervention. Also as used herein, the term "hyperoxic gas" refers to a gas with a partial pressure of oxygen greater than that of atmospheric air (e.g., PO2>0.20954 ATM), regardless of the pressure at which it is breathed (e.g., normobaric or hyperbaric). Dosage can be defined in terms of the frequency of treatments, the partial pressure of oxygen in inspired gas (PiO2), the duration of each treatment, and the number of treatments.

Further, the inventors of the present invention have determined that too high a dose of oxygen relative to the circumstances produces a suboptimal and in some cases, even a counterproductive outcome. In toxicological terms, this type of biphasic dose-response relationship is said to exhibit "hormesis" or to be "hormetic" in nature, characterized by a low dose stimulation or beneficial effect and a high dose inhibitory or toxic effect. In other words, in some circumstances, low doses of oxygen can be as effective as, or even more effective than, higher doses, even when these higher doses represent clinical norms. According to embodiments of the present invention, as the pathophysiology of the wound site improves during the course of therapy, the dose of oxygen can be adjusted (e.g., reduced) to optimize and/or maintain benefits. Thus, the present inventors have determined the efficacy of normobaric hyperoxia in the treatment of normal wounds such as cosmetic, oral/dental, hair transplant, and the like surgeries; prophylaxis against development of repetitive strain injuries such as carpal tunnel syndrome; neurological conditions such as traumatic brain injury, cerebral palsy, chronic traumatic encephalopathy, stroke and the like; developmental disorders such as autism spectrum disorders; inflammatory conditions such as glomerulonephritis; and unaccustomed physical use injury (e.g., delayed onset muscle soreness) when applied in appropriate doses.

In some aspects of the present invention, a significant issue relative to the practical application of low-dose oxygen was whether or not increased pressure as provided by any type of whole-body hyperbaric chamber is necessary to achieve positive outcomes. While the hyperbaric medical establishment maintains that pressure must be important because such low doses of oxygen as those provided in mild hyperbaric oxygen therapy (e.g., 24% O2 at 1.3 ATA) cannot be conceived of as having clinical benefit, the present inventors have determined the opposite is true; namely that hyperoxia, no matter how low the dose, and not pressure is the critical element of the therapy. Except in a few applications, hyperbaric pressure is essential only to provide greater inspired partial pressures of oxygen than can be achieved at normobaric pressure so that clinically effective doses of oxygen can be administered as required. Note that the exceptions relate to bubble disorders (e.g., decompression sickness, gas embolism) where hyperbaric pressure physically reduces gas bubble size according to Boyle's law and accelerates resolution of the gas phase by concentrating the molecules in a smaller volume.

The present inventors have further determined that after peak benefit is reached, greater doses of oxygen produce a progressively lower response which ultimately falls below that of no hyperoxic therapy at all. Consequently, the oxygen dose-response curve 102 shown in FIG. 1, which depicts a graph 100 of healing rate/quality versus oxygen treatment dosage, graphically expresses this hormetic relationship. The present inventors have determined that the outcome of hyperoxic therapy for a particular wound relates to the dose of oxygen delivered to that wounded tissue and not simply the gross, whole-body dose. Since oxygen not only has beneficial effects but is a toxic agent in relative overdose, the particular outcome of any hyperoxic therapy is the net result of the beneficial and toxic effects of oxygen at the wound site.

In some embodiments of the present invention, the consequences of the above determinations support the following conclusions. First, uncompromised wounds to a particular tissue can be treated optimally with lower doses of oxygen than wounds to this same tissue where oxygen delivery has been compromised by such things as circulatory disruption, edema, and inflammation. Second, as events such as angiogenesis and the reduction in edema and/or inflammation occur at a wound site, local oxygen delivery will increase and the optimal oxygen dose for therapy will decline correspondingly. Thus, the oxygen dose-response curve 102 will shift toward the left in the graph 100 of FIG. 1 over time as healing occurs. This has been validated through clinical trials of the methods of the present invention in the treatment of autism spectrum disorders.

Figure 2:
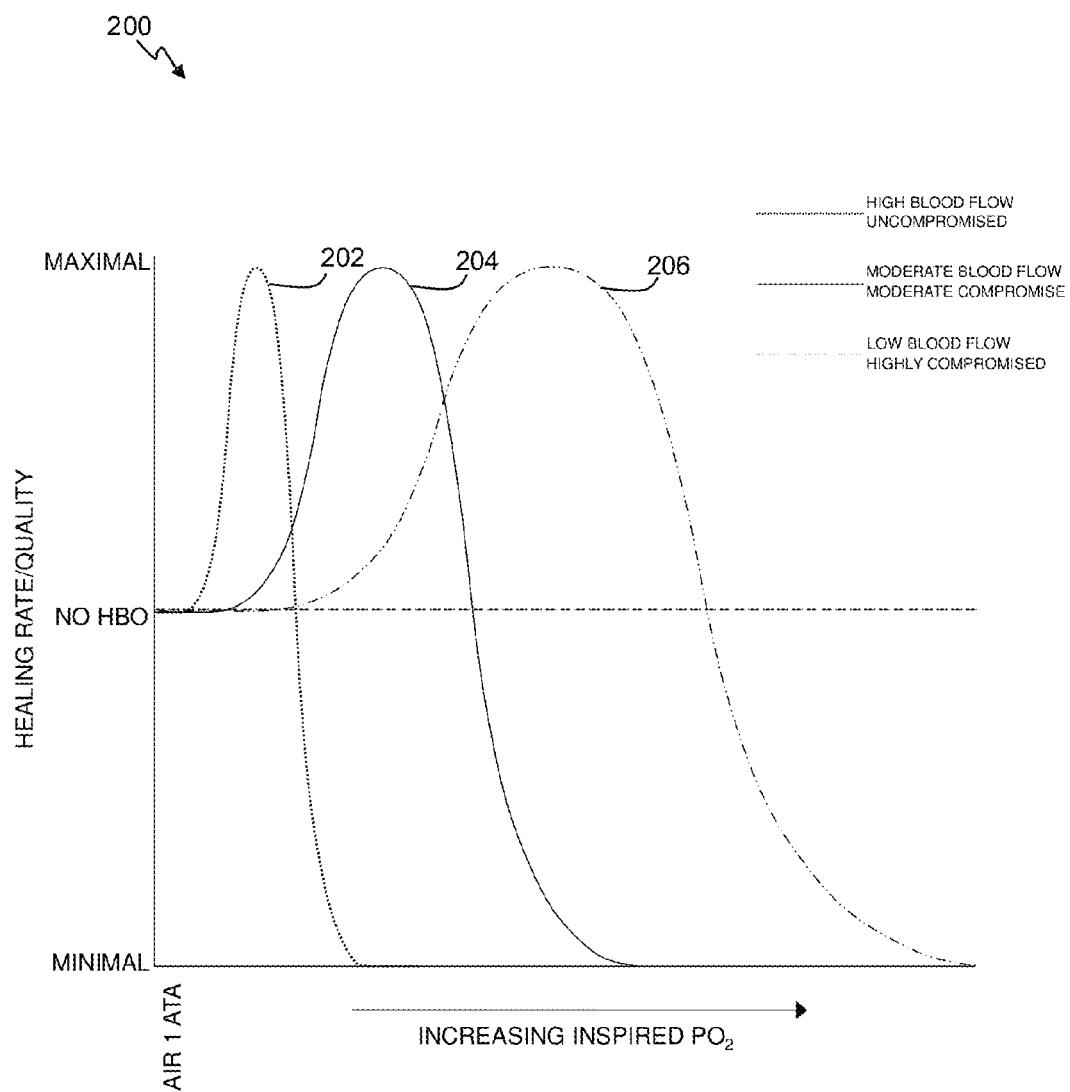
FIG. 2 is a graph of healing rate/quality versus oxygen treatment dosage for three different levels of tissue perfusion or tissue damage levels at the wound site according to some embodiments of the present invention.

A third conclusion drawn from the above states that where tissues have inherently different perfusion rates and, therefore, oxygen delivery rates, the tissue with the higher natural oxygen delivery rate will most often be optimally treated with lower doses of oxygen than other tissues. This determination provides the set of dose-response curves 202, 204, 206 shown in the graph 200 of FIG. 2. In other words, FIG. 2 illustrates a graph 200 of healing rate/quality versus oxygen treatment dosage for three different levels of blood flow and three different levels of how compromised the tissue was at the wound site. More specifically, the curves 202, 204, 206 represent differently wounded tissues where the leftmost dose-response curve 202 is for the least compromised tissue with the greatest perfusion rate and the rightmost dose-response curve 206 is for the most compromised tissue with the lowest perfusion rate. In terms of the oxygen dose-response model, the oxygen dose-response shifts toward lower doses as the blood flow to the wound site increases (e.g., more oxygen is delivered) and as the wound heals. Note that while local oxygen consumption will be a factor and could impose shifts in the curves for specific tissues, this fact does not change the basic nature of the relationships.

Figure 3:
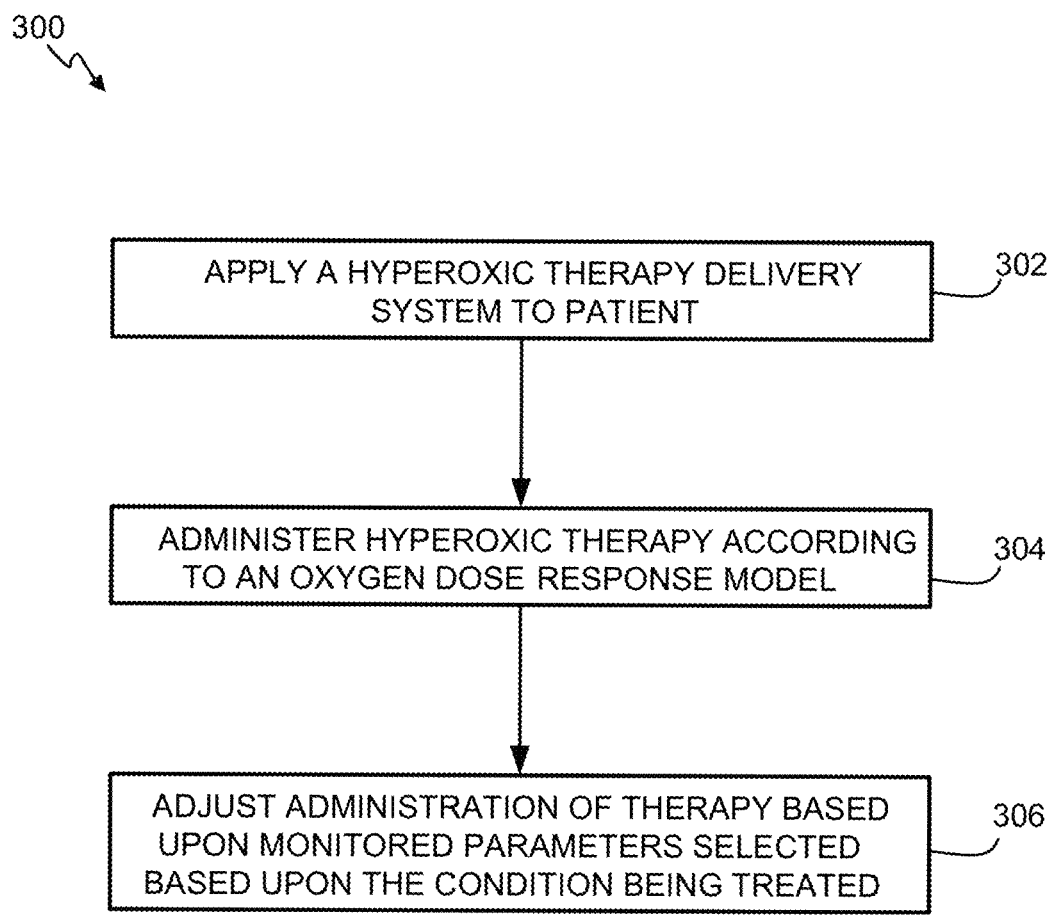
FIG. 3 is a flowchart depicting an example method of providing hyperoxic therapy according to some embodiments of the present invention.

Turning to FIG. 3, example methods of the present invention are described with respect to flowchart 300. In some embodiments, the inventive process of the present invention includes using a breathing apparatus (e.g., embodiments described below) or other medical device to enable a patient to receive hyperoxic therapy. Thus, some form of a hyperoxic therapy delivery system is initially applied to or put on the patient (302). Example embodiments of delivery systems particularly useful for performing the hyperoxic therapies of the present invention are described below, however, it should be understood that the methods of the present invention are not limited to the particular delivery systems described below. Hyperoxia is administered to the patient via the delivery system in accordance with an oxygen dose-response model (304). In other words, for example, the delivery system provides the patient with oxygen or other hyperoxic nitrogen-oxygen gas mix with a fraction of inspired oxygen (FiO2) of approximately 30% to approximately 100% and a fixed positive end expiratory pressure (i.e., the pressure in the breathing device above ambient) in the range of approximately 6 cm H2O to approximately 10 cm H2O (304). This small increased pressure is within the normal atmospheric variation of ambient pressure due to weather. The treatments can be conducted at local (e.g., normal) atmospheric pressure, a nominal 1 ATA (atmospheres absolute). Whole-body pressure chambers are not required and increased hydrostatic pressures are not required. In some embodiments, for example, an initial starting dose would involve treatments of 90% FiO2 administered approximately once per day for up to approximately five days per week for eight weeks with a treatment session duration in the range of approximately 30 minutes to approximately 90 minutes. The dose will vary based upon the patient and the condition. For example, the treatment plan (which specifies the initial dose) for a child with autism might be for a period of one year whereas the plan for an adult with an elective surgery wound can be for a one week period.

As the therapy process progresses, particularly in chronic cases, the oxygen dose of the treatments (i.e., FiO2, duration, and/or frequency of treatments) is adjusted (306). As noted above, as the therapy process progresses the oxygen dose-response curve 102 (FIG. 1) generally shifts to the left and the peak healing rate/quality occurs at a lower inspired PO2.

In some embodiments, the adjustments will include a reduction in the FiO2, duration, and/or frequency of treatments in accordance with the oxygen dose-response model, to maintain effectiveness. Such adjustment can be based on assessment of monitored parameters and the parameters can be selected based upon the condition being treated. For example, in the case of autism, the monitored parameters can include the total and sub-scale scores of the Autism Treatment Evaluation Checklist developed by Bernard Rimland and Stephen M. Edelson of the Autism Research Institute (see Magiati I et al., J Intellect Disabil Res 2011; 3(55):302-312) which is hereby incorporated herein by reference. The adjustments are applied recursively to dynamically maintain the optimal healing rate/quality.

In the case of Traumatic Brain Injury (TBI), the monitored parameters can include, for example, scores from the Immediate Post-concussion Assessment and Cognitive Testing (ImPACT® Applications) as described by Lovell M R, Iverson G L, Collins M W, Podell K, Johnston K M, Pardini D, Pardini J, Norwig J, and Maroon J C, in the publication entitled "Measurement of symptoms following sports-related concussion: Reliability and normative data for the post-concussion scale," Appl. Neuropsychol, 2006; 13:166-174 which is hereby incorporated herein by reference. Additionally or alternatively, the score from the Post-traumatic Disorder Check List (PCL) in its various forms including civilian and military by Weathers F W, Litz B T, Herman D S, Huska J A, and Keane T M, in the publication "The PTSD checklist: Reliability, validity, & diagnostic utility" which was a paper presented at the Annual Meeting of the International Society for Traumatic Stress Studies, San Antonio, Tex. in 1993 (see Weathers F W, Litz Bt, Keane T M, Herman D S, Steinberg H R, Juska J A, Kraemer H C. The utility of the SCL-90-R for the diagnosis of war-zone related posttraumatic stress disorder. J Trauma Stress 1996; 9(1):111-128) which is hereby incorporated herein by reference.

In the case of Cerebral Palsy (CP), monitored parameters can include, for example, scores from the Gross Motor Functional Measure (GMFM) by Nordmark E, Jarnlo G B, and Hagglund G, described in the publication "Comparison of the Gross Motor Function Measure and Pediatric Evaluation of Disability Inventory in assessing motor function in children undergoing selective dorsal rhizotomy" in Dev Med Child Neurol, 2000; 42:245-252, which is hereby incorporated herein by reference.

In the case of glomerulonephritis, monitored parameters can include, for example, a measure of the level of serum creatinine as further explained at the Cleveland Clinic Meded website (see also Winter C C. Kidney function tests in children. Calif Med 1961; 94:127-131) may be used and is hereby incorporated herein by reference.

An example therapy process for acute cases, such as may occur during aesthetic cosmetic surgery, can include an initial treatment with an oxygen dose that is relatively high (e.g., having a relatively long treatment duration for example, in the range of approximately 60 to 90 minutes) followed by a number of additional treatments (e.g., in the range of approximately two to nine) of relatively shorter durations (e.g., in the range of approximately 45 to 60 minutes). In acute surgery cases where only diminishment of swelling and bruising is desired for example, one 90-minute treatment can provide sufficient results in some embodiments. In other embodiments, different therapy processes in accordance with the present invention that include different parameters or parameter values can be used.

Figure 4:
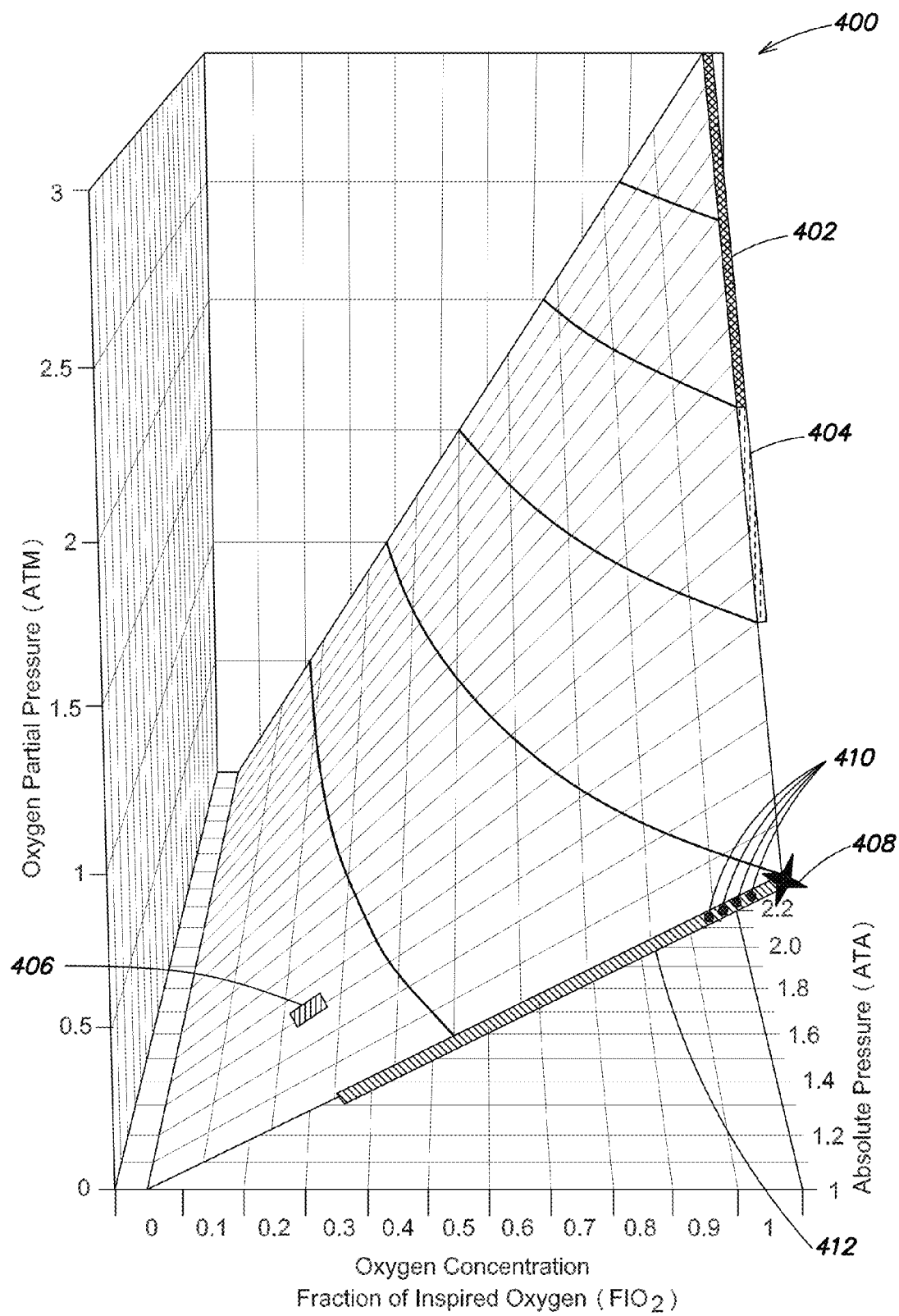
FIG. 4 is a three dimensional graph depicting the operating ranges for treatment parameter values of various prior art hyperoxic therapies relative to values for the novel hyperoxic therapy of embodiments of the present invention.

Although several aspects of embodiments of the present invention have been disclosed above with respect to the novel features of the invention, it should be understood that there are numerous prior art hyperoxic therapies that can include one or more treatment parameter values that may incidentally and/or temporarily overlap with the novel "adjusting low-dose oxygen" hyperoxic therapy of embodiments of the present invention. In an effort to better clarify the differences between embodiments of the present invention and the prior art hyperoxic therapies, the following table and FIG. 4 are provided.

| HYPEROXIC THERAPY | ABSOLUTE PRESSURE (ATA) | OXYGEN CONCEN- TRATION (%) (FiO$_2$) | PARTIAL PRESSURE OF OXYGEN (ATM) | CONDITIONS TREATED |
|---|---|---|---|---|
| Conventional HBO$_2$ | 2.0-3.0 | 100 | Static in the range 2.00-3.00 | FDA recognizes those conditions recommended by the Undersea and Hyperbaric Medical Society (UHMS) HBO$_2$ Therapy Comm. |
| Off-label HBO$_2$ | 1.5-2.0 | 100% | Static in the range 1.50-2.00 | Neurological conditions; sports injuries (based on empirical results); Lyme disease |
| Mild HBO$_2$ | 1.3 | 21%-28% | Static in the range 0.27-0.36 | Neurological conditions |
| Hospital-based emergency-care and advanced-first-aid-based oxygen therapy | 1.0 | 100% | Static at 1.00 | Resuscitation, major trauma, anaphylaxis, major hemorrhage, shock, active convulsions, hyperthermia, and transient hypoxaemia (e.g., pulmonary embolism) |
| Home-and care-facility-based oxygen therapy | 1.0 | 90 ± 3% | Static in the range 0.87-0.93 | Increasing arterial PO$_2$ in COPD; controlling breathlessness in end-stage cardiac or respiratory failure, advanced cancer, or neurodegenerative disease |
| "Adjusting-low-dose oxygen" hyperoxic therapy of embodiments of the present invention | 1.0 | 30%-100% | Adjusted over the range of 0.30-1.00 | Chronic neurological & other medical conditions such as inflammatory disorders; developmental disorders; enhanced healing in elective surgery; repetitive strain injury; unaccustomed use injury; prophylaxis against repetitive strain injury |

As can be seen from the above table wherein each row represents a different type of hyperoxic therapy and the last row describes embodiments of the present invention, some of the prior art therapies include treatment parameter values that incidentally and/or temporarily overlap with the values of embodiments of the present invention. This can be more clearly seen in the three dimensional chart 400 depicted in FIG. 4. The area patterned in crosshatching corresponding to yellow color represents the treatment parameter value range for conventional hyperbaric oxygen (HBO$_2$) treatment 402. The area patterned in crosshatching corresponding to purple color represents the treatment parameter value range for off-label HBO$_2$ treatment 404. The area patterned in crosshatching corresponding to orange color represents the treatment parameter value range for mild HBO$_2$ treatment 406. The point denoted by a star represents the treatment parameter values for hospital-based emergency-care and advanced-first-aid-based oxygen treatment 408. The points denoted by four dots represent the treatment parameter values for home-based and care-facility-based oxygen treatment 410. The area patterned in crosshatching corresponding to green color represents the treatment parameter value range for "adjusting low-dose oxygen" hyperoxic treatment 412 of embodiments of the present invention.

Even where prior art methods overlap with the treatment parameter values of embodiments of the present invention and/or the conditions being treated however, there are two very significant distinctions: (1) the treatment parameter values of embodiments of the present invention are adjusted through a progression wherein the oxygen dose (i.e., either treatment frequency, treatment duration, and/or inspired oxygen concentration (FiO2)) is reduced periodically according to the oxygen dose-response model as compared to the static values in the prior art therapies, and (2) where the pressure range overlaps, the treated conditions are different and where the treated conditions overlap, the treatments are conducted at normal atmospheric pressure and not under hyperbaric conditions in a whole-body chamber. Embodiments of the present invention provide a form of systemic hyperoxic therapy which is conducted at normobaric pressure without the need for a whole-body pressure chamber. Unlike with other prior art systemic hyperoxic therapies, the apparatus used in the present invention to supply the hyperoxic gases and deliver them to the patient are suitable for use in private homes with the assistance of relatives or caregivers of the patients, in care facilities with the assistance of their typical staff, and in physicians' offices with the assistance of nurses or technicians. For such assistance, specialized clinical training is not required. Simple basic training in how to safely and effectively use the equipment to administer the hyperoxic therapy of the present invention in accordance with the prescription of a physician is all that is required.

Prior art oxygen therapy (i.e., normobaric oxygen therapy) differs from embodiments of the present invention. In such prior art therapy, oxygen is administered systemically for acute conditions in emergency medical and advanced first aid situations for resuscitation, major trauma, anaphylaxis, major hemorrhage, shock, active convulsions, hyperthermia, and transient hypoxemia (e.g., pulmonary embolism). Oxygen is also administered to firefighters suffering smoke inhalation and divers suffering decompression sickness and/or gas embolism prior to their reaching a recompression chamber. This therapeutic process is called "oxygen therapy."

Oxygen, or much more commonly, now, gas from medical oxygen concentrators, typically with an oxygen concentration of 90±3%, is administered systemically in home and care facility settings to increase arterial PO2 in chronic obstructive pulmonary disease (COPD) and to alleviate breathlessness in end-stage cardiac or respiratory failure, advanced cancer, or neurodegenerative disease. This process is also called "oxygen therapy," though in dealing with breathlessness, it has been shown that the actual partial pressure of oxygen may not be important.

The oxygen concentration of the gas breathed by the patient is a function of the flow rate of oxygen, typically ranging from 2 to 15 standard liters per minute (slpm), and the type of delivery device utilized. Such devices typically include a nasal cannula delivering between 24-40% oxygen; a simple face mask delivering between 28-50% oxygen; an air-entrapment or Venturi mask delivering a graded concentration of oxygen up to 40%; a partial rebreathing mask delivering from 40-70% oxygen; a tight-fitting non-rebreather mask delivering from 60-80% oxygen; a humidified, high-flow nasal cannula delivering up to 100% oxygen, so long as the patient breathes exclusively through his nose. Depending on the reason for oxygen therapy, the therapy gas may be breathed continuously for extended periods (e.g., days).

This type of "oxygen therapy" which also called "surface oxygen," unlike embodiments of the present invention, is not administered to enhance normal wound healing including those from elective surgical procedures, repetitive strain injuries, and delayed onset muscle soreness; to heal or permanently improve chronic conditions such as neurological injury, developmental disorders, and inflammatory disorders; or to prevent the development of pathological conditions such as repetitive strain injury. Embodiments of the present invention involved systemically administering hyperoxic treatments (that are adjusted periodically) which are efficaciously used for all of these conditions. Consequently, there is no overlap in applications for embodiments of the present invention and prior art normobaric oxygen therapy. Since embodiments of the present invention use gas with an oxygen concentration ranging from approximately 30% to approximately 100% at 1.0 ATA, however, there is partial overlap in the partial pressures of oxygen used for conventional "oxygen therapy" and embodiments of the present invention.

Prior art hyperbaric oxygen therapy (HBO$_2$) differs from embodiments of the present invention. Hyperbaric oxygen therapy involves the systemic administration of hyperoxic gas in a whole-body pressure chamber at a pressure greater than that of the normal ambient environment (i.e., >1.0 ATA (atmospheres absolute)). The gas breathed ranges from 100% oxygen to air, the latter rendered hyperoxic because of the increased pressure in the chamber. The partial pressure of oxygen (PO2) is equal to the fraction of oxygen in inspired gas (FiO2) multiplied by the absolute pressure in the whole-body chamber in ATA (PA). This equation can be expressed as:

$$PO_2 = FiO_2 \times P_A$$

HBO$_2$ may be divided into several categories related to the type of whole-body chamber utilized, the chamber pressure utilized, and the conditions treated. These different forms of HBO$_2$ are described and contrasted with the therapy of embodiments of the present invention below.

Three types of whole-body chambers are used for the administration of HBO$_2$. These are multiplace chambers which can accommodate multiple occupants and, for clinical use, have pressure ratings from 3.0 ATA for rectangular-cross-section chambers to 6.0 ATA or more for circular-cross-section chambers; monoplace chambers which accommodate only one occupant and commonly have a pressure rating of 3.0 ATA; and Gamow bags or Gamow-bag equivalents which can have FDA clearance, for the treatment of acute altitude sickness but have come to be used for a hyperoxic therapy called "mild hyperbaric oxygen therapy" (mHBO$_2$), commonly at a pressure of 1.3 ATA.

Multiplace chambers are compressed with air, and oxygen or another treatment gas is breathed by patients via tight-fitting demand masks with an overboard dump (e.g., exhaled gas passes through an exhaust regulator and out of the chamber and into a receiver or out of the building), or from flow-through hoods. The hood exhaust is also carried out of the chamber and into a receiver or out of the building. It is important that exhaust gas from either masks or hoods is taken out of the chamber as an increasing oxygen concentration in a multiplace chamber would impose significantly increased risk of fire.

Monoplace chambers are typically compressed and flushed continuously with oxygen, and the patient breathes the chamber atmosphere without a breathing device. As a consequence, these chambers are designed, manufactured, operated, and maintained to strict safety codes and standards so that they do not present an inordinate risk of fire.

Mild hyperbaric oxygen chambers are reinforced fabric, inflatable devices often with a zipper closure, and with limited visibility into and out of the chamber through relatively small window inserts. They have been modeled after equipment of a sort that was originally developed to manage acute altitude sickness (i.e., "Gamow bag," so named after its inventor, Rustem Igor Gamow). These chambers typically have a pressure rating of 1.3 ATA and are inflated and flushed with gas from an oxygen concentrator providing 24% to 28% oxygen. The patient usually breathes the chamber atmosphere. Such devices are not designed for the many off-label clinical applications of mHBO$_2$ for which they have come to be promoted. Where they are cleared by the FDA, it is as being substantially equivalent to the Gamow bag with an "indications for use" statement specifying treatment of acute mountain sickness. The FDA requirements for such devices do not necessitate that they meet any gas purity standards or engineering safety standards for pressure vessels (which is how they are being used in m $HBO_2$).

Prior art conventional hyperbaric oxygen therapy differs from embodiments of the present invention. Conventional $HBO_2$ is conducted in hospital-associated, dedicated clinical units using either multiplace or monoplace hyperbaric chambers. Treatment pressures commonly range from 2.0 ATA to 2.8 ATA and 100% oxygen is invariably the treatment gas breathed by the patients. The treatments are conducted by specially trained chamber operators and a physician must be in attendance (i.e., in close proximity throughout the treatments).

Primarily because of third-party reimbursement issues, these dedicated clinics will only treat indications recognized by the Centers for Medicare & Medicaid Services (CMS). These are the applications, and only those applications, for hyperbaric oxygen therapy advocated by the Undersea and Hyperbaric Medical Society (UHMS). They currently consist exclusively of:
  Air or gas embolism
  Carbon monoxide poisoning/carbon monoxide poisoning complicated by cyanide poisoning
  Clostridial myositis and myonecrosis (gas gangrene)
  Crush injury, compartment syndrome, and other acute traumatic ischemias
  Decompression sickness
  Arterial insufficiencies
    Central retinal artery occlusion
    Enhancement of healing in selected problem wounds
  Severe anemia
  Intracranial abscess
  Necrotizing soft tissue infections
  Osteomyelitis (refractory)
  Delayed radiation injury (soft tissue and bony necrosis)
  Compromised grafts and flaps
  Acute thermal burn injury
  Idiopathic sudden sensorineural hearing loss
Chronic conditions treated over prolonged courses of therapy (e.g., osteomyelitis, problem wounds) employ the same dose of oxygen (i.e., static pressure-duration-frequency combination) for all treatment sessions from the beginning of therapy to its end. This has been the case from the inception of $HBO_2$ to the present time.

Note that none of the indications advocated by the UHMS are normal wounds of any type; neurological injury; developmental or inflammatory disorders; or prophylaxis to prevent the development of any pathological conditions. Consequently, there is no overlap in applications of prior art conventional $HBO_2$ and embodiments of the present invention. Since embodiments of the present invention use gas with an oxygen concentration ranging from approximately 30% to approximately 100% at approximately 1.0 ATA, there is also no overlap in the partial pressures of oxygen used for conventional hyperbaric oxygen therapy and embodiments of the present invention.

Prior art off-label hyperbaric oxygen therapy differs from embodiments of the present invention. Off-label $HBO_2$ is conducted in free-standing clinical units using either multiplace or monoplace whole-body hyperbaric chambers. Treatment pressures commonly range from 1.5 to 2.0 ATA, though occasionally pressures as high as 2.4 ATA are used, and 100% oxygen is invariably the treatment gas breathed by the patients. Treatments are conducted by specially trained operators and a physician may or may not be in attendance.

These clinics are operated on a private-pay basis, and for the most part, are prepared to treat any condition for which there is some rationale and a patient is willing to pay. Common applications include neurological injuries such as cerebral palsy (CP), stroke, and traumatic brain injury (TBI); developmental disorders such as autism spectrum disorders (ASD); sports injuries which are classified as normal wounds; inflammations such as Crohn's disease. In a very few cases, cosmetic surgeons have monoplace chambers in their offices and use $HBO_2$ to enhance the healing of their surgical procedures. Given these applications, there may be overlap between the uses of off-label $HBO_2$ and embodiments of the present invention. However, $HBO_2$ by definition is conducted in a whole-body chamber at increased pressure with PO2>1 atm while embodiments of the present invention are conducted at normal atmospheric pressure without the use of a whole-body chamber and with PO2≤1 atm. Further, treatments for chronic conditions (e.g., neurological injuries, developmental disorders) in off-label $HBO_2$ invariably employ a constant dose of oxygen (i.e., a static pressure-duration-frequency) for the entire course of treatments (e.g., all treatment session use the same dose of oxygen). There is no systematic adjustment in dose, much less adjustments based on oxygen does-response model, even from one course of treatments for a given condition to subsequent courses of treatments for that same condition.

Prior art mild hyperbaric oxygen therapy differs from embodiments of the present invention. Mild $HBO_2$ is conducted on an exclusively off-label basis in patients'homes, physicians' offices, and in free-standing clinics. Treatment pressures are typically 1.3 ATA which is the maximum pressure rating of the device. Users are not required to have any special training.

Common applications include neurological conditions such as CP, multiple sclerosis, TBI, and stroke; developmental disorders such as ASD; and sports injuries. The chambers are purchased or rented by the users, or services are obtained through "clinics" on a private-pay basis. Courses of therapy (e.g., treatment sessions) employ the same dose of oxygen (i.e., static pressure-duration-frequency) from start to finish. Embodiments of the present invention and mHBO₂ can overlap in the treatment of a variety of neurological conditions. There is also overlap in PO2 at the low end range of embodiments of the present invention, but mHBO₂ is always conducted at a hyperbaric pressure while embodiments of the present invention is conducted at normobaric pressure with gases having higher concentrations of oxygen than those typically used for mHBO₂.

As mentioned above, embodiments of the present invention have some applications in common with both off-label hyperbaric oxygen therapy and mild hyperbaric oxygen therapy. However, in addition to the differences in treatment parameter values and the adjustments made in accordance with the oxygen does-response model, there are very significant differences in the convenience, cost, and safety of off-label and mild hyperbaric oxygen therapy processes in comparison to embodiments of the present invention.

The cost of the monoplace or multiplace chambers and their installations, specially trained staff, clinic facility, direct physician involvement, oxygen consumed, and chamber and facility maintenance in off-label clinics mean that the charge for treatments at such clinics are significant. As off-label hyperbaric clinics are not common, getting to them can require significant travel. In the best of cases, given round trip travel, time for the patient to change out of his street clothes into clinic-provided attire (for fire safety), compression time, treatment time, and decompression time, treatments can consume four hours a day or more, five days a week for the course of therapy, typically 20 or 40 treatments costing on the order of $4,000 to $8,000, respectively.

Other issues involved in hyperoxic therapy conducted in whole-body chambers at an HBO2 clinic include having to accommodate one's schedule to that of the clinic's; confinement, with confinement anxiety and sometimes true claustrophobia as complications; limitation in activities over the course of treatment; chamber pressurization or compression to treatment pressure which necessitates that the patients equalize the pressure in their middle ears and sinuses or suffer discomfort, pain, ruptured blood vessels, and even ear drum rupture from barotrauma if this common complication is not effectively managed by the chamber operator; chamber depressurization or decompression to surface pressure which subjects the chamber occupants to risk of serious barotrauma such as gas embolism should gas be trapped in their lungs, particularly during events such as emergency decompression (e.g., because of a fire in the chamber room); development of absorption atelectasis (e.g., lung collapse resulting from oxygen absorption from alveoli with reduced or absent gas exchange), which has been reported in the treatment of a stroke case, as no provisions are now taken to prevent atelectasis in treatments conducted with breathing hoods or masks in multiplace chambers and none can be taken for treatments conducted in monoplace chambers, so long as the patients breathe the chamber atmosphere without a breathing device. As a consequence of such factors, patient compliance (i.e., unwillingness to take the hyperbaric hyperoxic treatments) was reported to be a major issue in a study of HBO2 for stroke.

Because of the hyperoxic environments in both oxygen-flushed monoplace and air-compressed multiplace chambers, fire safety is an extremely important concern in HBO2 of any sort.

In regards to the use of HBO2 for the enhanced healing of wounds from elective surgical procedures, a multiplace chamber installation would be much too costly and space consuming. Thus, such an installation would have to be based on monoplace chambers. Even then, these clinical hyperbaric chambers are expensive to purchase and install (e.g., on the order of $150,000-$200,000 for a single monoplace chamber, room preparation, and essential liquid oxygen supply system), require office space that is usually not available within a cosmetic surgery suite (e.g., a dedicated space of approximately 20'×10' for a single monoplace chamber and additional space in the office or outside the building for a sizable liquid oxygen supply system), and the employment of a qualified chamber operator. In view of the cost factors and the requirement for space that would not usually be available in a physician's offices, the use of HBO2 as an adjunct hyperoxic therapy for such purposes would not be cost-effective and could rarely even be physically accommodated.

In comparison, the therapy of embodiments of the present invention is easily accommodated and conducted when convenient in the homes of patients, the facilities where the patients are being cared for, or in the offices of physicians where elective surgical procedures have been performed. As will be discussed below, the apparatus of the present invention is self-contained and can be used in a relatively small space (e.g., on the order of 25 square feet or less including space for a comfortable chair for the patient to sit in during treatment.). During treatments, patients are free to engage in almost any activity possible within the reach of the hood umbilical. These include watching TV, listening to music, playing games, reading, working on a computer, and writing.

As whole-body pressure chambers with changes in pressure are not involved in embodiments of the present invention, there are no requirements for equalizing pressure in gas spaces such as the middle ear and sinuses, no risk of decompression barotrauma such as gas embolism, and no confinement issues. Positive measures have also been taken to prevent absorption atelectasis so it is not a risk factor for embodiments of the present invention.

In regards to risk of fire, since oxygen is involved, this is an important issue, and proper fire safety guidelines must be followed at all times. With the system operating at only 1 ATA, however, there is no exacerbation of the problem by having pressurized hyperoxic gases in confined spaces. There is also limited oxygen storage with liquid oxygen cylinders as the gas source, and no oxygen storage when medical oxygen concentrators are the gas source. These factors further minimize the hazard of fire. Consequently, despite the widespread use of liquid oxygen cylinders and, more recently, medical oxygen concentrators for oxygen therapy outside of medical establishments, oxygen-enriched fire incidents are rare.

In contrast to off-label hyperbaric oxygen therapy for overlapping applications, the therapy of embodiments of the present invention is less costly, more convenient, less restrictive, and safer. Embodiments of the present invention also incorporate dose adjustments to maintain therapy effectiveness which HBO2 protocols do not.

In regards to cost, rental rates for the smaller mHBO2 chambers and the system of embodiments of the present invention are not greatly different. The larger mHBO2 chambers are more expensive, however. In practical use, mHBO2 is much more confining and more limiting in activities during treatments than the system of the present invention.

From a safety standpoint, embodiments of the present invention have considerably less risk than mHBO2. A patient in an mHBO2 chamber cannot get out of the device on his own. He requires outside assistance. Consequently, should there be a failure of the gas supply for any reason (e.g., electrical power failure, oxygen concentrator failure, or supply line disconnect), then an improperly supervised patient could die from carbon dioxide poisoning and/or hypoxia.

In contrast, as will be discussed below, the system of embodiments of the present invention includes a relief valve to provide room air flow into the hood should the supply system fail. In addition, in embodiments where an oxygen concentrator is used as the gas supply source, a loud audible alarm system is provided for detectable failures (e.g., electrical power failure, low supply pressure, etc.).

Another safety issue in regards to mHBO2 chambers is structural integrity. As noted in the description of these chambers above, since they are regarded as substantially equivalent to the Gamow bag by the FDA, they are not required to meet any engineering safety standards for 510(k) clearance. In order to be eligible for FDA 510(k) clearance, the new device must exhibit roughly the same safety and effectiveness characteristics as the "predicate" device to which the new one is being compared. Not surprisingly, therefore, some mHBO2 chambers, in particular one that actually does have FDA clearance, have failed multiple times in service creating what the FDA has classified as a "life-threatening" incident.

With respect to elective surgical procedures, mHBO2 has no efficacy, and the zipper bags utilized for mHBO2 lack adequate patient-friendliness for this market, even if the therapy did provide benefit.

In summary, mHBO2 involves treatments in confining, whole-body pressure chambers with limited visibility and little patient-friendliness. Compression to treatment pressure requires equalization of middle ear and sinus pressures with operator mismanagement potentially leading to discomfort, pain, and overt injury (e.g., ear drum rupture). As the chamber environment is breathed by the patient without a delivery device, there can be no provision for the prevention of absorption atelectasis. The chambers, themselves, are subject to structural failure which could lead to life-threatening incidents, and no safety features are built in to mitigate against obvious failure situations. The process of mHBO2 has no provision for change of dose correlated with patient progress.

In contrast, therapy in accordance with embodiments of the present invention is conducted at normal atmospheric pressure and does not require compression. The system is not confining and permits patients to engage in a great variety of routine activities. Because the system utilizes only a very small pressure to prevent absorption atelectasis, there is no risk of injury due to catastrophic pressure boundary failure. Lastly, the process of embodiments of the present invention includes provision for dose changes in response to patient progress to maintain treatment effectiveness.

Figure 5:
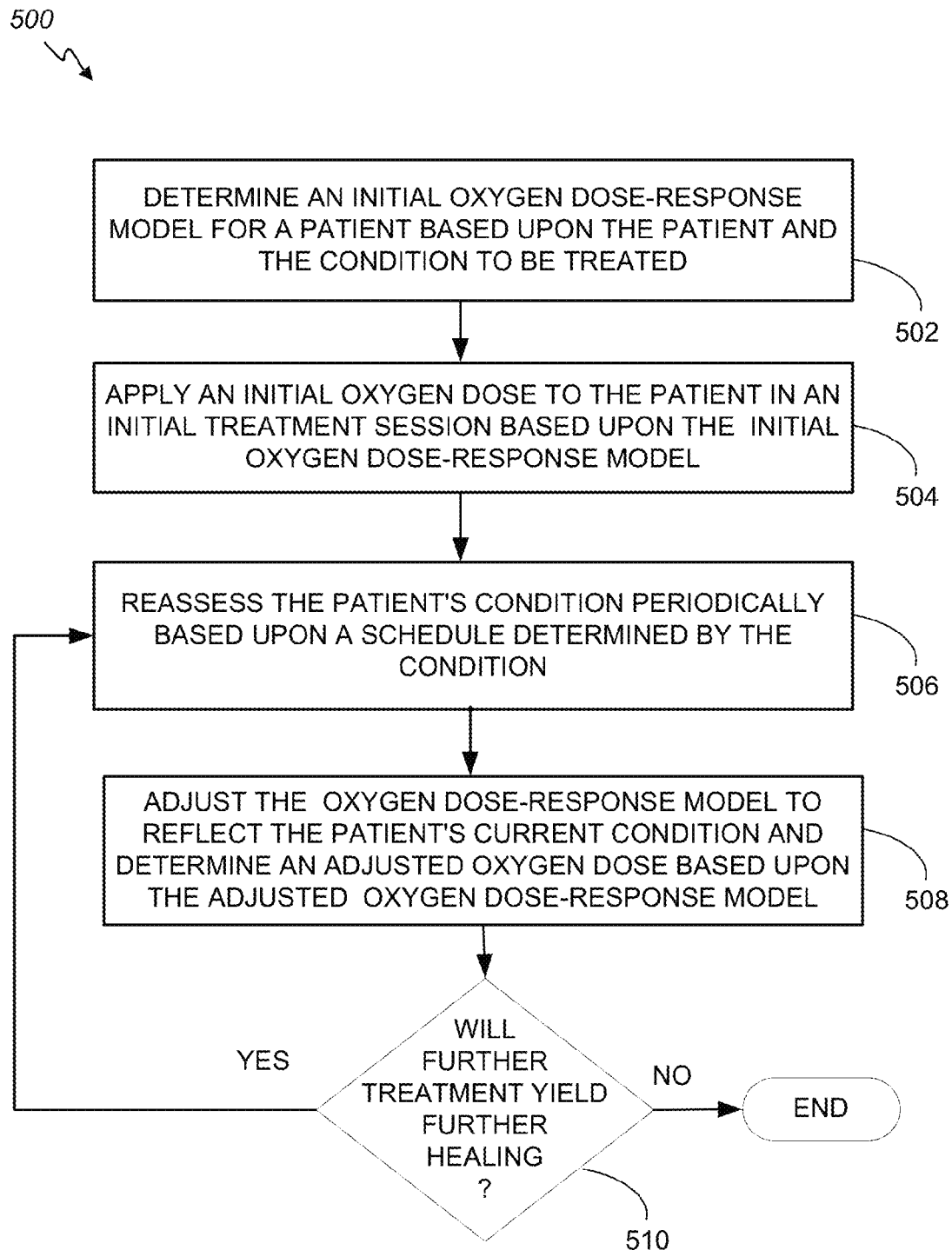
FIG. 5 is a flowchart depicting a second example method of providing hyperoxic therapy according to some embodiments of the present invention.

Turning now to FIG. 5, a flowchart depicting a second example method 500 according to embodiments of the present invention is depicted. An initial oxygen dose-response model is determined for a patient based upon the patient and the condition to be treated (502). The oxygen dose-response model can include a curve that identifies an optimal oxygen dose for maximal healing rate and quality. The oxygen dose can be defined in terms of pressure (e.g., inspired PO2 within a predefined envelope of absolute pressure (ATA), oxygen concentration, and oxygen partial pressure ranges), duration (e.g., length of the treatment session, and frequency (e.g., number of treatment sessions per time period, for example number per week, number per month, etc.).

The initial dose is applied to the patient in an initial treatment session (504). A reassessment of the patient's condition is made periodically based upon a schedule determined to optimize treatment of the condition (506). The oxygen dose-response model is adjusted to reflect the patient's current condition and an adjusted oxygen dose is determined based on the adjusted oxygen dose-response model (508). A determination is made whether further treatment sessions will provide further healing (510). For example, if the treated condition is healed, if normal levels of monitored indicators are achieved, or if no further improvements have been achieved since a prior determination, the endpoint of treatment is deemed to have been reached. If further treatment sessions will provide further healing, the method 500 returns to assessing the patient's condition (506). If further treatment sessions will not provide further healing, the method 500 ends.

The hyperoxic therapy delivery system of embodiments of the present invention is one which permits the slightly-greater-than ambient pressure within the system to be comfortably maintained and tolerated over the course of the treatment. Because a conventional continuous positive airway pressure (CPAP) mask which provides the requisite gas delivery capability must be strapped securely to the face of the patient, it is not physically ideal for the administration of the inventive hyperoxic therapies described above, particularly in the case of children and patients with facial wounds. Likewise, the cost, space requirements, and operational requirements including gas supply, staffing, risk, and maintenance of multiplace hyperbaric chambers, and even monoplace chambers, a Gamow bag, or any of the other soft-skinned hyperbaric chambers, may make hyperoxic therapy administered using a chamber impractical. Consequently, in some embodiments, the present invention can include the use of a novel breathing hood which includes enhanced gas flow distribution within the hood and enhanced ease-of-use features such as hood application, securing, and removal.

Removing the need for close facial contact (such as with a CPAP mask) not only makes the hyperoxic gas delivery system of the present invention more comfortable, but also improves compliance in patients, such as autistic spectrum (ASD) patients, and eliminates problems and complications for patients in the cosmetic, hair transplant, and dental surgery sectors who have had facial or head procedures.

Compared to conventional breathing hoods, the hyperoxic gas delivery system of the present invention has improved comfort, an improved gas flow pattern within the hood to enhance carbon dioxide (CO2) clearance and minimize internal temperature buildup, includes a fail-to-safety inward opening relief valve for loss or failure of gas supply, improves the ease of putting the device on and taking it off the patient, and overpressure prevention. The hood assembly of the present invention is designed so that the clear flexible plastic head cover (hood/tent), the elastic neck dam and the torso collar each incorporate molded O-ring finishes which allow them to be replaceable, and the ring elements can be sterilized/disinfected and reused from patient to patient.

Figure 6:
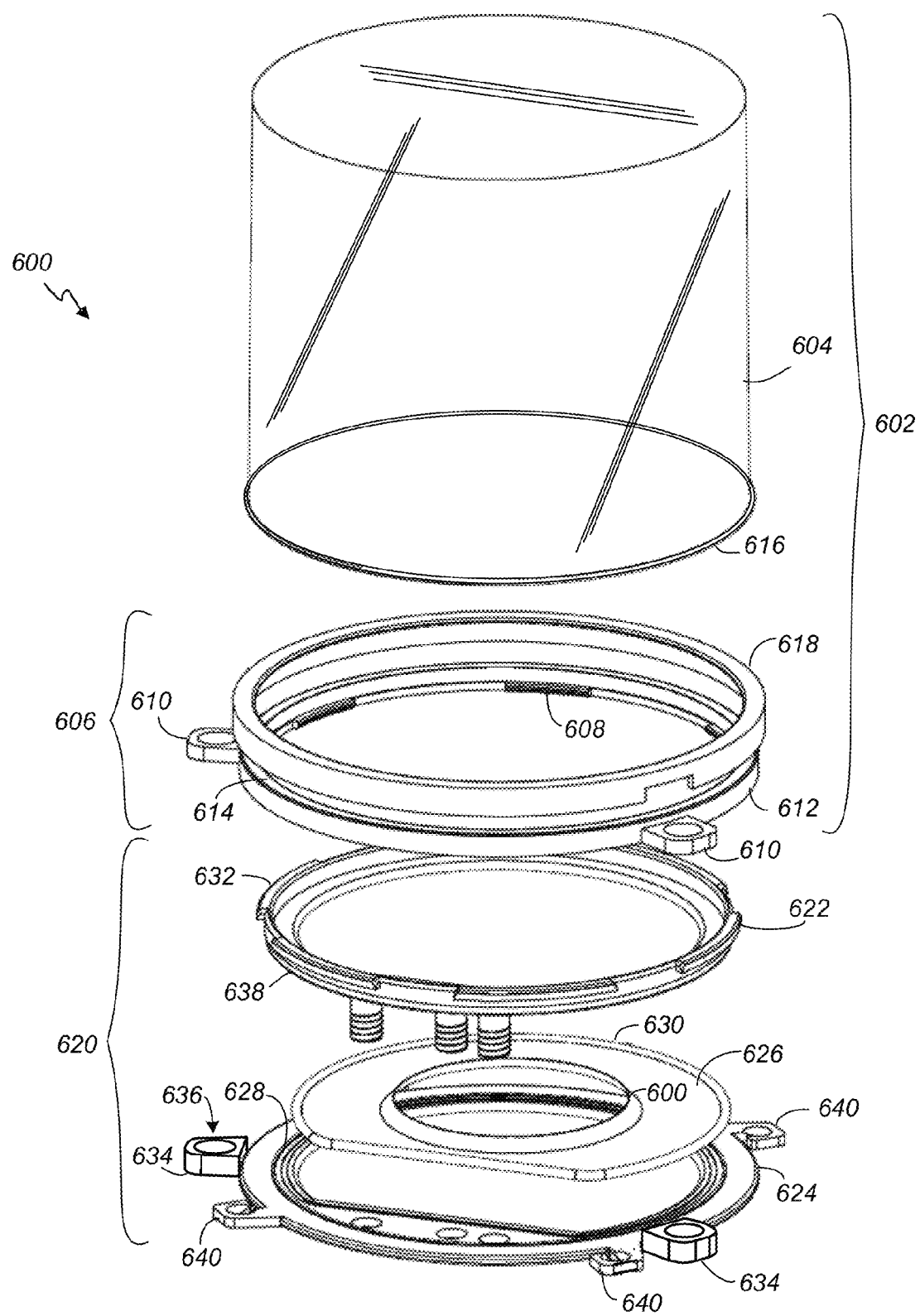
FIG. 6 is an exploded perspective view of an example hood assembly of a hyperoxic gas delivery system in accordance with embodiments of the present invention.

In some embodiments, the hyperoxic gas delivery system of the present invention includes six main elements. Turning to FIG. 6, the first main element is the hood assembly 600 which is depicted in an exploded perspective view. The hood assembly 600 includes a sealed "head tent" that covers the head of the patient creating the enclosed environment from which the patient breathes the hyperoxic gas. The hood assembly 600 may include two parts. The first, an over-the-head portion 602, can be formed from soft, clear plastic head tent 604 which takes the general shape of a bell jar/bucket when fully inflated. At the bottom of the over-the-head portion 602 is a hood ring 606 with internal interrupted threads 608 and external lugs 610. The hood ring 606 of the over-the-head portion 602 can include two parts, an inner ring 612 which has a circumferential O-ring groove 614 on its outer diameter that will engage with a circular molded O-ring finish 616 on the head tent 604 of the over-the-head portion 602. The O-ring finish 616 of the head tent 604 is sealingly trapped and secured when the second part of the hood ring 606, an outer ring 618 is placed over the inner ring 612 and secured with removable distributed (e.g., evenly spaced about the circumference) pins (not shown) which engage with the inner ring 612. In alternative embodiments, the distributed pins may be replaced with alternative fixings such as screwed elements, twist-locks, or some other fixing.

The second part of the hood assembly 600 is the neckseal ring assembly 620. The neckseal ring assembly 620 can include an upper part 622 and a lower part 624 that together capture and securely hold a neck dam 626. A groove 628, sized and shaped to accommodate a non-circular molded O-ring finish 630 of the neck dam 626 (and torso collar sleeves (not shown)) is provided in the lower part 624 of the neckseal ring assembly 620. In some embodiments, the upper part 622 of the neckseal ring assembly 620 has interrupted threads 632 on its outside diameter that engage with the interrupted threads 608 on the inside diameter of the hood ring 606, and external lugs 634 and tabs 640. The lugs 634 with finger holes 636 and markings (not shown) are positioned to guide the caregiver/technician when fitting and removing the hood assembly 600.

The lugs 610, 634 are provided in pairs, one pair on each side of the outer circumference of the hood ring 606 and neckseal ring assembly 620. One lug 610 of each pair is on the hood ring 606, the other lug 634 of each pair is on the neckseal ring assembly 620. When the hood ring 606 is placed on to the neckseal ring assembly 620, one pair of lugs 610, 634 will be together (e.g., immediately adjacent to each other or in contact), the other pair will be separated. Squeezing the separated pair of lugs together rotates the hood ring 606 on the neckseal ring assembly 620 engaging the interrupted threads 608, 632 and locking the two rings 606, 620 together. This rotation also separates the originally pair of lugs used to orient the hood ring 606 and the neckseal ring assembly 620 during initial placement on the patient.

To unlock and remove the over-the-head portion 602, the now separated pair of lugs 610, 634 is squeezed together, thus rotating the hood ring 606 in the opposite direction and unlocking it from the neckseal ring assembly 620. Note that in some embodiments, the lugs 634 on the neckseal ring assembly 620 can extend upward (e.g., have an increased thickness compared to the lugs 610 on the hood ring 606) such that when a pair of lugs 610, 634 are squeezed together, each lug 634 on the neckseal ring assembly 620 serves as a positive stop for the corresponding lug 610 on the hood ring 606, ensuring that the interrupted threads 608, 632 are properly aligned (or misaligned) and fully engaged (or fully disengaged). In alternative embodiments, each pair of lugs 610, 634 is adapted to align vertically when squeezed together to provide a positive indication that the interrupted threads 608, 632 are properly aligned (or misaligned) and fully engaged (or fully disengaged).

In operation, this closure also activates an "O"-ring seal located in a groove 638 provided on the outer circumference of the neckseal ring assembly 620 immediately below the interrupted thread 632. This O-ring seal prevents gas leakage from the hood assembly neckseal joint between the hood ring 606 and the neckseal ring assembly 620. In this way, the hood assembly 600 is either securely locked in place, ready for use, or unlocked for removal.

The tabs 640 on the neckseal ring assembly 620 include "L" or "J" shaped slots which are used in securing the hood assembly 600 so it does not tend to float up on the patient's head when in service.

In some embodiments, there are alternative approaches to preventing gas leakage from the neckseal ring assembly-patient interface during treatment. The first uses a conventional elasticized neck dam (similar in function to the neck dam in the breathing hood manufactured by AMRON International, Inc. of Vista, Calif.). In contrast to prior art neck dams, the neck dam 626 of embodiments of the present invention is designed to be replaceable and the outer edge is finished with a non-circular molded O-ring 630 compatible with the non-circular groove 628 provided in the lower part 624 of the neckseal ring assembly 620. The neck dam 626 of the present invention is compressionally engaged in the non-circular O-ring groove 628 when the upper part 622 and lower part 624 of the neckseal ring assembly 620 are brought together and secured by screwed elements (not shown) or, in alternative embodiments, fixings such as twist locks, spring clips, or other fasteners. An opening in the center of the elastic neck dam 626 is cut to size to seal securely around the patient's neck and prevent gas leakage. To help provide a secure seal on the neck and reinforce the neck dam material against tearing, a series of concentric circumferential O-rings are molded into the neck dam. When used properly, these seals have a long life.

Figure 7:
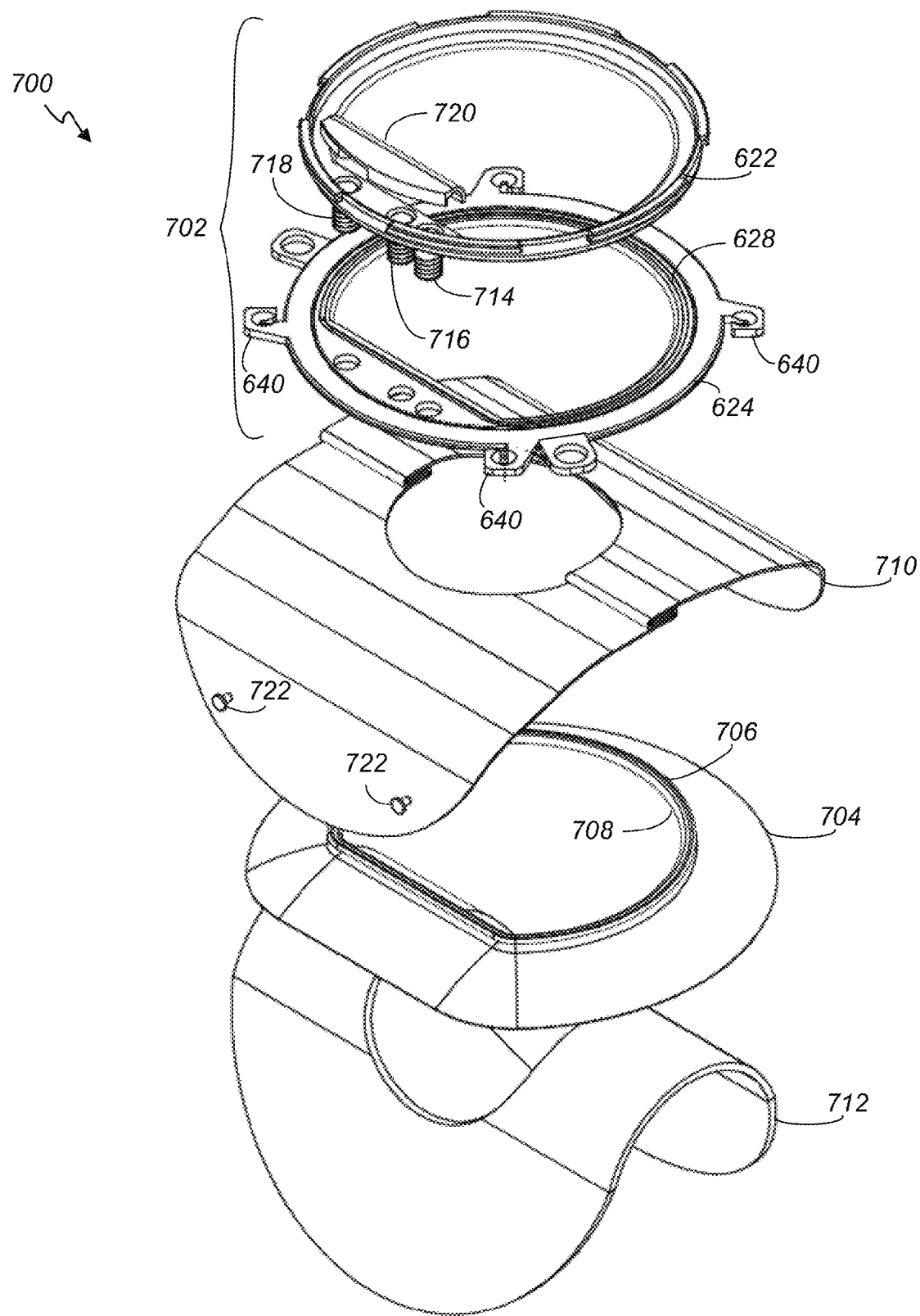
FIG. 7 is an exploded perspective view of an example torso collar assembly of a hyperoxic gas delivery system in accordance with embodiments of the present invention.

Turning now to FIG. 7, a second, alternative embodiment uses a torso seal or torso collar assembly 700 that is open to the full inside diameter of the lower part 624 of the neckseal ring 702 and does not have any elements that fit tightly around the neck (e.g., no neck dam 626 as in the embodiment of FIG. 6). Rather, this alternative embodiment includes parts that effectively seal the over-the-head portion 602 around the patient's upper chest, upper back, and shoulders. One part is a molded torso collar 704 which is finished with a non-circular molded O-ring finish 706 which adapted to engage with the non-circular O-ring groove 628 on the lower part 624 of the neckseal ring 702.

The torso collar 704 is highly compliant and conforms to the shape of the patient's upper torso. Extending from the inside opening of the torso collar 704 is a flexible sleeve 708 that ends in the non-circular molded O-ring finish 706 that can be inserted into and retained by the non-circular O-ring groove 628 provided in the lower part 624 of the neckseal ring 702. The non-circular molded O-ring finish 706 of the torso collar 704 is compressionally engaged in the non-circular O-ring groove 628 when the upper part 622 and lower part 624 of the neckseal ring 702 are brought together and secured by screwed elements (not shown) or, in alternative embodiments fixings such as twist locks, spring clips, or other fasteners.

After the torso collar 704 is lowered over the patient's head (with the neckseal ring 702 up) and is resting on his shoulders, a two-piece securing collar 710 as shown in FIG. 7, is put over the torso collar 704 to hold it snuggly in place and ensure retention of the seal against the patient's skin. The securing collar 710 is in turn held in place by a hood assembly harness. The over-the-head portion 602 (FIG. 6) is then put in place and sealed by rotating the hood ring 606 on the neckseal ring 702 of the torso collar assembly 700 as above.

The torso collar assembly 700 is specifically designed for those, such as cosmetic surgery patients, who cannot tolerate anything tight passing over the face or head, or being around the neck. In some embodiments, a padded collar (not shown) in the form of a circular tube joined, for example, with Velcro™ and shaped like a "donut" can be opened out so that it can be placed around a patient's neck. The padded collar can be filled with liquid gel, fine beads or air so that it readily conforms to the shape of the torso collar 704 resting on the patients upper torso. In some embodiments, the padded collar can be placed in between the torso collar 704 and the securing collar 710 and can be used to provide additional downward pressure on the torso collar 704 to affect a seal. In some embodiments, an optional support collar 712 can be placed over the head and on to the shoulders to support and spread the load and ensure the torso collar assembly 700 can be fitted comfortably to the widest possible of range of subjects.

In some embodiments, three service ports 714, 716, 718 are provided in the neckseal ring assembly 620 and neckseal ring 702 respectively of the two types of sealing assemblies, one each for the gas supply 716 and exhaust 718 hoses, one for the hood assembly mounted inward-opening relief valve 714. These service ports 714, 716, 718 are located in the front (i.e., face side) of the neckseal ring assembly 620/ neckseal ring 702 immediately below the mouth and nose of the patient. The inward-opening relief valve 714 lifts in the case of low pressure in the hood caused by a failure of the primary gas supply, and will allow ambient air to flow into the hood assembly.

The service ports 714, 716, 718 are covered by a cowling 720 that serves at least three purposes: (1) to protect the service ports 714, 716, 718 mechanically; (2) to help prevent contamination from patient-generated sources such as spittle; and (3) to impose directionality to the hood assembly gas circulation. Directionality of gas flow is achieved by means of shaped compartments within the cowling 720 that are finished with radiused ends and divided by a centrally located internal bulkhead in the cowling 720 that separates the incoming gas flow paths from the exiting gas flow paths. This gives directionality to the gas circulating within the hood assembly, forcing it to flow in one direction around the patients head to exhaust on the other side. In this way, a circumferential flow pattern is established within the hood assembly to ensure that $CO_2$, as well as excess heat and moisture are carried away to optimize patient comfort and safety. The cowling 720 additional helps to avoid irritation and drying of the patient's eyes by preventing the incoming gas from flowing directly into the patient's face. In some embodiments, on the underside of the neckseal ring 702, the inward opening relief valve, supply, and exhaust service ports 714, 716, 718 are finished in male spigots. Each of the supply 716 and exhaust 718 spigots are threaded to engage with the female threaded nut and ferrule terminations on an umbilical (not shown). The threads can be different to prevent inadvertent cross-connection.

Unlike conventional breathing hoods currently used to deliver oxygen to patients in multiplace hyperbaric chambers which are intended to be disposable, in some embodiments, a feature of the hood assembly of the present invention is reusability, longevity and reliability in service. This is achieved in two ways: the male/female locking parts of the hood assembly are durable and tolerant to normal wear and tear, and the soft, "consumable" elements of the hood assembly such as the elasticized neck dam 626, the clear plastic head tent 604, and the torso collar 704, are relatively inexpensive and easily replaceable by a technician or caregiver/parent through the use of the two-part retaining rings 606, 620, 702.

The more permanent parts of the hood assembly 600 such as the neckseal ring 702 and hood ring 606 and the securing collar 710, on the other hand, can be taken apart for cleaning and disinfection in order to maintain general cleanliness or in preparation for use by new patients. In this way, reusability, reliability and longevity in service are provided.

In some embodiments, when in use with a slightly positive pressure inside it, the hood assembly 600 may tend to ride up on the patient's head. Thus, the present invention can include a securing mechanism to hold down the hood assembly 600 and prevent it from bothering the patient. The hood assembly 600 can be secured using one or more approaches as described below. These approaches are fully adjustable and can be employed based on the type and size of the patient. For small children, additional shoulder padding can be provided to ensure that the hood assembly is comfortable to wear. Note that the securing mechanism attaches to the neckseal ring assembly 620 (or neckseal ring 702) so that the neckseal ring assembly 620 (or neckseal ring 702) can be fitted and comfortably secured to the patient before the over-the-head portion 602 is placed on the patient.

In some embodiments, a first example securing system 800 is provided that uses balls 802 (e.g., approximately 25 mm in diameter) on adjustable lengths of elasticized cords and/or suspenders 804 (called, "bungee-balls") that individually fit into shaped slots in each of the four tabs 640 (FIGS. 6 & 7) positioned approximately ninety degrees apart on the circumference of the neckseal ring assembly 620 and neckseal ring 702. The suspenders 804 can include fasteners 806 (e.g., clips, hooks, snaps, loops, etc.) at the end opposite the balls 802 to secure to the patient's clothing or studs 722 on the securing collar 710. This arrangement provides a snug but not tight (e.g., not uncomfortable or restrictive) tie-down that has passive automatic adjustability when the patient changes body position. Once the neckseal ring assembly 620 or neckseal ring 702 is in place on the patient with a neck dam 626 or a torso collar 704, the four balls 802 are fitted into their respective slots in the tabs 640 on the neckseal ring assembly 620 or neckseal ring 702 and secured to the patients clothing or the studs 722 on the securing collar 710. Then, when the hood ring 606 is placed on the neckseal ring assembly 620 or neckseal ring 702, because of the nature of the slots and the size of the balls 802, the latter are physically locked in place and cannot be released until the head tent 604 is removed.

Figure 9:
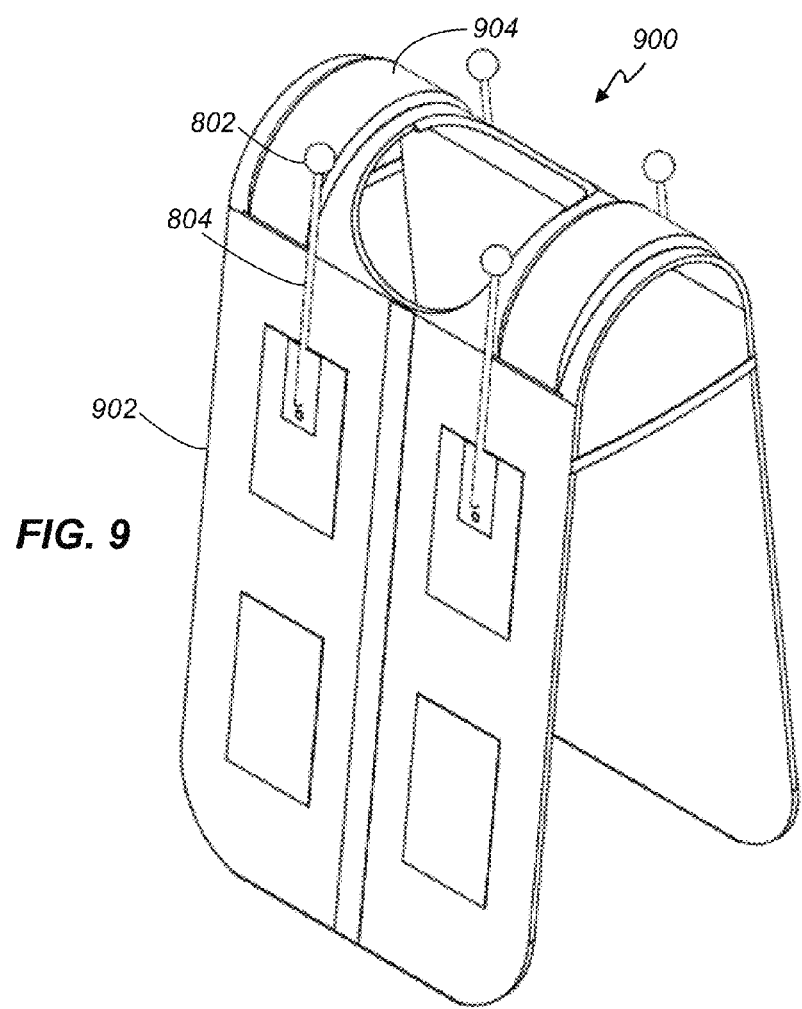
FIG. 9 is a perspective view of a second example securing system of a hyperoxic gas delivery system in accordance with embodiments of the present invention.

This design provides a significant convenience and safety feature that helps ensure the hyperoxic gas delivery system is properly secured before treatment and remains in place while the unit is in use. As depicted in FIG. 9, in some embodiments, a second example hood assembly securing system 900 can include a loose-fitting, adjustable over-jacket 902 similar to the brightly colored safety jackets worn by many workers. To counter the natural lift that comes when the hood assembly is in service, the ball 802 and suspenders 804 are attached to this over-jacket which is fitted with small weighted inserts that are strategically placed to optimize comfort and ensure the weight is evenly distributed around the hood assembly neckseal ring assembly 620 or neckseal ring 702. As useful, shoulder pads can be fitted to provide cushioning 904 between the shoulders and the hood assembly neckseal ring assembly 620 or neckseal ring 702.

Figure 8:
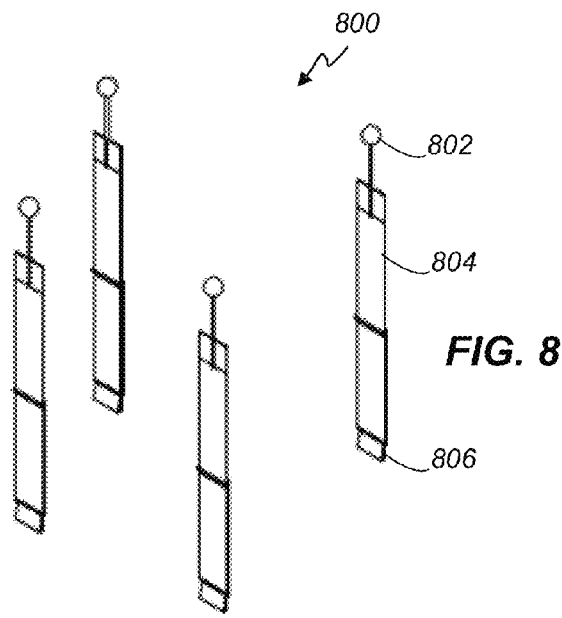
FIG. 8 is a perspective view of a first example securing system of a hyperoxic gas delivery system in accordance with embodiments of the present invention.

In some embodiments, four individually fitted adjustable, elasticized suspenders as shown in FIGS. 8 and 9 finished with ball 802 end fittings as discussed above may be used to secure the hyperoxic gas delivery system. Each suspender can be 2-inches wide and fitted with standard suspender fasteners 806 at the bottom end designed to attach to the over-jacket 902 or alternatively directly to the patient's waistband of a skirt or pants including those of typical hospital scrubs and gowns. This method of fitting minimizes contact with the torso that some patients, such as those who have undergone breast or abdominal surgery, may not tolerate well.

The hyperoxic gas delivery system of the present invention is designed to go over the head of patients without coming into contact with the head and/or face. The underside of the neckseal ring assembly 620 or neckseal ring 702 is designed to sit on the shoulders and has wide flat surface that prevents point loads and ensures any pressure (weight) is dispersed over a wide area rather than concentrated. For very small children, a support collar 712 can be provided to interface with the underside of the neckseal ring 702, to reduce the effective open diameter of the neckseal ring 702 and maintain good contact with the shoulders, thus helping to avoid any physical discomfort. The support collar 712 is designed so that it can conform to the contour of the upper torso and shoulders front to back but is stiff enough laterally across the shoulders to support the hood assembly neckseal ring 702 even when it is only making partial contact with the patient's shoulders. This is achieved by creating a material sandwich with center stiffening using either corrugation or simple straw-like tubular elements. The top of each pad includes a Velcro™ finish that will attach to a Velcro™ strip applied to the underside of the hood assembly neckseal ring 702. In this manner, simple systems are provided that are highly adjustable to fit a wide range of patients, and practical for use even on difficult or non-compliant patients.

The inventors recognize that the hyperoxic gas delivery system of the present invention may be used with certain types of patients who, due to the nature of their condition, such as autism spectrum disorder (ASD), may be inherently less compliant and difficult to manage. To provide distraction and fun for such patients, soft, translucent, and colorful, covers and/or gels that will fit over or attach to the head tent 604 (FIG. 6) and impart a variety of themes such as a space helmet or cartoon characterizations can be provided as an option. The material of manufacture will ensure these covers will naturally adhere to the clear plastic material of the head tent 604 without need for adhesive, thus also be easily removed and reusable.

Figure 10:
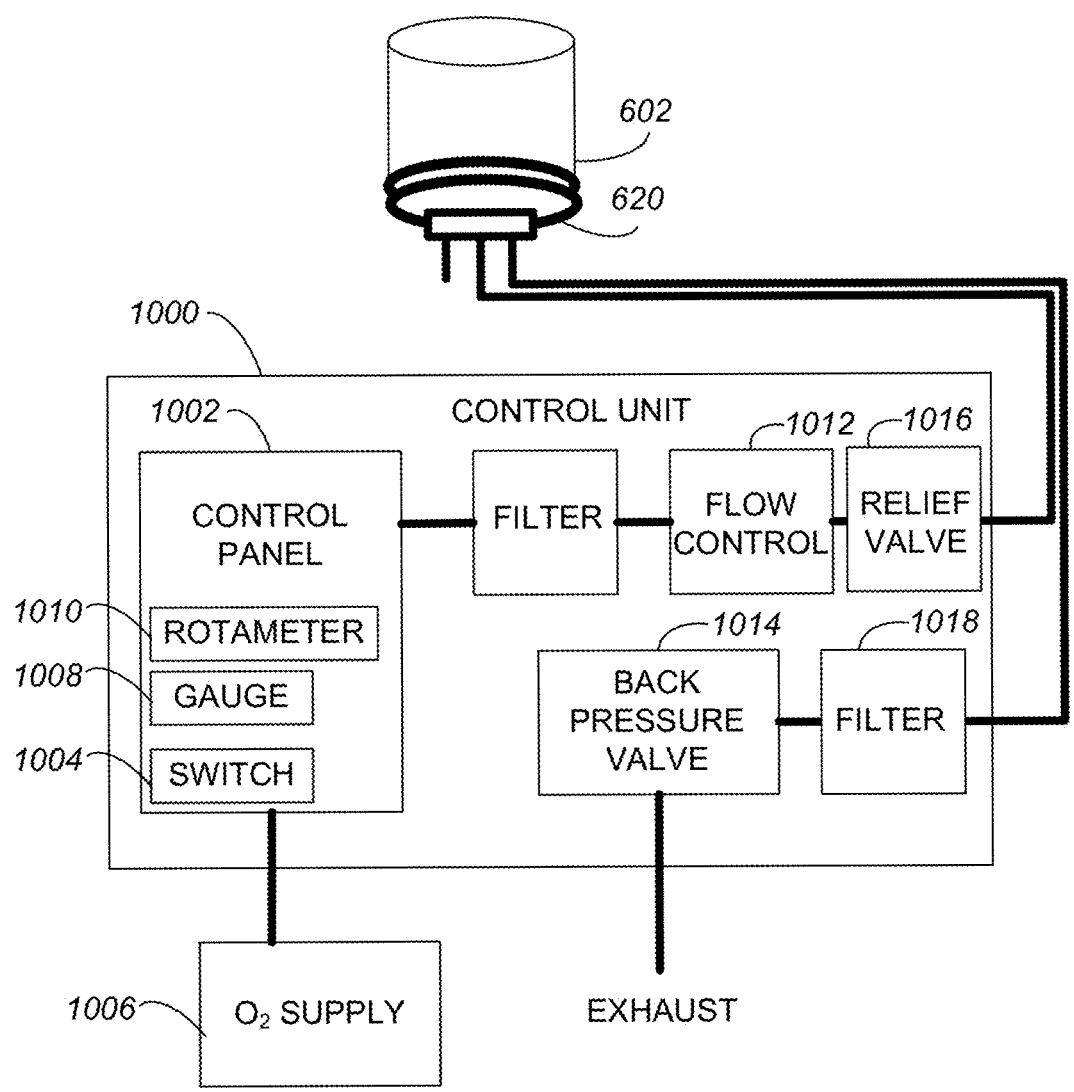
FIG. 10 is a block diagram of an example hyperoxic gas delivery system in accordance with embodiments of the present invention.

Turning now to FIG. 10, the hyperoxic gas delivery system control unit 1000 provides for control of all functions of the hyperoxic gas delivery system using a clearly labeled panel 1002. In one embodiment using liquid cylinder storage oxygen is turned on and off with a covered fail-to-safety switch 1004. System activation is achieved by lifting the switch cover and toggling the switch 1004 to the open position which brings oxygen flow to the neckseal ring assembly 620 (or neckseal ring 702). The over-the-head portion 602 is fitted to the neckseal ring assembly 620 after oxygen is on-line and removed before oxygen flow is shut-down. Shut-down is by a single action—just closing the cover. In other embodiments, the switch 1004 actuates a concentrator 1006 which brings hyperoxic gas on line to the neckseal ring assembly 620 (or neckseal ring 702). The over-the-head portion 602 is fitted to the neckseal ring assembly 620 (or neckseal ring 702) after oxygen is on-line and removed before oxygen flow is shut-down. There is a gauge 1008 which shows pressure in the hood assembly 600 during all stages of the respiratory cycle. A rotameter 1010 (e.g., flow meter) is provided to show the flow-rate into the hood assembly 600 at all times. Flow rate is set by adjusting the rotameter 1010 or selecting the appropriate control valve settings on the liquid oxygen storage cylinders or oxygen concentrator flow meters 1012. A pre-set back-pressure valve 1014 inside the hyperoxic gas delivery system control unit 1000 controls the hood assembly exhaust pressure, and thus internal pressure. An overpressure relief valve 1016 is located in the supply circuit that will open and prevent the hood assembly 600 from being over-pressurized in the highly unlikely event of a failure in the exhaust circuit. An in-line particulate filter 1018 on the exhaust side protects a back-pressure valve 1014 from any excess moisture or particulates coming from the hood assembly 600. The back-pressure valve 1014 is set at a fixed pressure ranging from approximately 6 cmH2O to approximately 10 cmH2O which produces a greater functional residual capacity (FRC) in the patient's lungs and helps to ensure that an adverse pulmonary effect known as absorption atelectasis (i.e., lung collapse due localized oxygen absorption) will not occur when the patient is breathing hyperoxic gases. Data in the published literature has established that a residual pressure of 6 cmH2O is the minimum value needed to prevent atelectasis. Atelectasis is a safety concern since it has been shown to occur in patients breathing hyperoxic gases at both normobaric and hyperbaric pressures.

Figure 11:
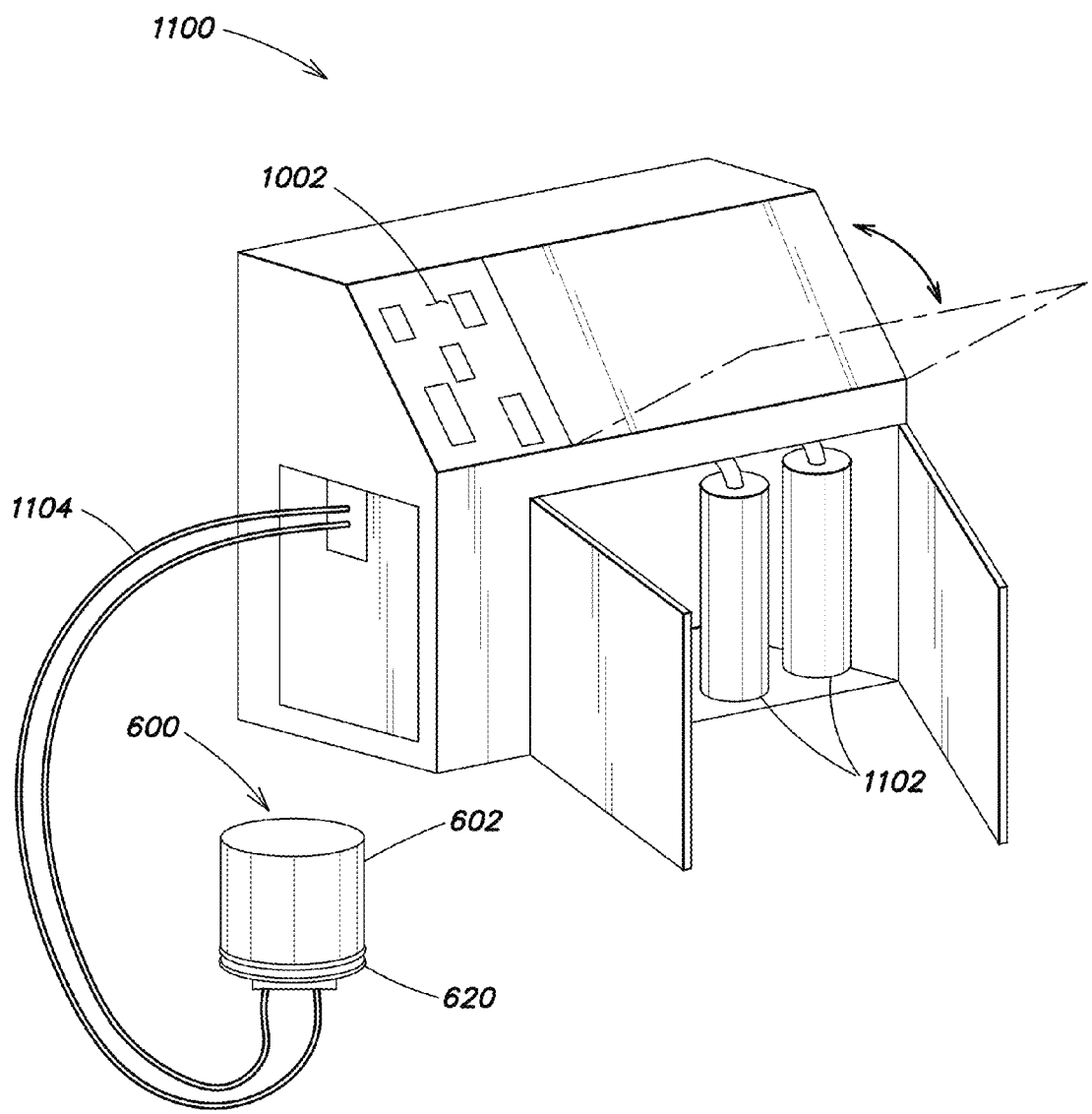
FIG. 11 is a perspective view of an example hyperoxic gas delivery system in accordance with embodiments of the present invention.

The hyperoxic gas delivery system storage cabinet 1100 as shown in FIG. 11 houses all of the elements necessary to operate the system. These include the hyperoxic gas delivery system control unit 1000 and panel 1002, the gas supply source 1102, and an umbilical 1104. It also provides storage space for the hood assembly 600 and the umbilical 1104 when not in use. The cabinet 1100 can be designed to look like a piece of furniture, presented in either traditional or contemporary styles to be suitable for use in a home or professional office. These options help ensure that the cabinet 1100 fits reasonably well into any décor. The cabinet 1100 can be split into several separate compartments, each of which can be independently lockable to ensure equipment can be kept safe and secure while not in use. In some embodiments, the lower compartment accommodates liquid gas storage cylinders with full width double doors to permit easy handling and exchange. A removable horizontal bracket (i.e., stretcher) can be provided for structural support and to secure the cylinders in an upright position during normal use. In some embodiments, the hyperoxic gas is supplied from an oxygen concentrator and the lower compartment is used to house and protect the concentrator. A gas connection manifold can be located on the inside rear wall of the lower section to connect the oxygen source to the hyperoxic gas delivery system control panel 1002.

In some embodiments, the upper section of the cabinet 1100 contains the hyperoxic gas delivery system control panel 1002 and a storage space with a drop-down door which can also be used as a writing/work surface. The height of the storage space provides secure storage for the hood assembly 600, spare parts (e.g., neck dams), and the hyperoxic gas delivery system control panel.

The supply and exhaust umbilical 1104 (i.e., the supply and exhaust gas hose assembly) connects the hood assembly 600 to the hyperoxic gas delivery system control panel 1002. The umbilical 1104 can be embodied as a simple twin-hose assembly contained in a sleeve. The large-bore flexible hoses utilized ensure that the umbilical 1104 can be made into virtually any reasonable length to permit the patient to move freely within an area determined by the caregiver. This can be an important compliance factor for ASD patients. In alternative embodiments, the umbilical 1104 may include a hose-in-hose (e.g., concentric) format in which a larger bore outer hose contains a smaller bore inner hose effectively forming a single hose umbilical which is easier to handle and store. For example, the outer hose can serve as the exhaust while the inner hose serves as the supply, each having its own end connector that will engage with single gas supply/exhaust spigot on a modified neckseal ring.

The gas supply and exhaust pipework from the hyperoxic gas delivery system control panel 1002 is terminated inside an inset "locker" space provided in the cabinet 1100 and located to allow easy connection/disconnection of the umbilical 1104. A circumferential support bracket or self-winding reel located inside the locker allows the umbilical 1104 to be coiled and stowed securely. This ensures the treatment area can be kept tidy and the umbilical 1104 protected from damage when not in use. The locker door can be notched to allow it to be closed while the umbilical 1104 is deployed.

In some embodiments, the flow of gas used by the hyperoxic gas delivery system in operation is on the order of approximately 20 to approximately 30 SLPM (standard liters per minute) provided by oxygen concentrators and/or liquid cylinders. In some embodiments, this kind of demand can be most effectively served from a liquid source or an oxygen concentrator rather than a compressed-gas source (i.e., high pressure cylinders). Liquid and/or concentrator based oxygen supply systems designed and approved for home or physician office use are available in a number of sizes. For example, liquid oxygen supply systems provided by CAIRE® and Puritan Bennett and/or oxygen concentrators such as those manufactured by Chart Industries can be utilized. Because of the regulatory limitations on oxygen supply volume (i.e., <3,000 SCF) without special safety provisions unlikely to be found routinely in either a home or a physician's office, the possibilities for manifolding cylinders to maximize service life between refills are limited. With any industrial or medical gas application it is desirable to minimize the frequency of cylinder refills. The travel time and labor involved in refills can be the most expensive elements in the cost. The Liberator 45 model manufactured by CAIRE®, a Chart Industries Company, provides an efficient option for storing liquid oxygen. These cylinders have been designed for routine home use and can be easily be manifolded together. To facilitate handling on-site, each cylinder can be mounted on a roller base.

As described above, oxygen dose (e.g., a function of treatment duration, oxygen partial pressure, and frequency) is a primary factor in achieving the optimal response to therapy. This has been demonstrated in ongoing ASD trials where adjusting dose has effectively kept progress moving forward when it became suboptimal. Further, neurological conditions, in general, respond better to lower partial pressures of oxygen when being treated with hyperbaric oxygen therapy. This is a function of the very high blood flow to the brain and the sensitivity of that organ to the metabolic and other disruptions relatively high doses of oxygen can produce.

Even further, some neurological conditions such as Alzheimer's, particularly in its early stages, may be more effectively managed at normal atmospheric pressure with oxygen concentrations lower than 100% than with pure oxygen. Consequently, it is desirable to establish a practical and cost-effective means of supplying nitrogen-oxygen mixes to patients with a regulated concentration of oxygen (e.g., 60%, 80%, etc.).

While gas companies can supply nitrogen-oxygen mixes to order in high-pressure cylinders, neither the cost nor the storage aspects of such supply are likely be tenable for personal applications. Thus, methods and apparatus for injecting nitrogen or preferably air into the breathing circuit have been developed so that pure oxygen is diluted with nitrogen to the extent desired. At the low oxygen flow rates used in the present invention, the volumes and flow rates of the diluent gas are relatively small. A system employing a high-quality pressure regulator and a series of fixed-orifice Venturi valves that can be configured to entrain surrounding air and deliver the required mixture at a fixed injection rate can suffice.

The hyperoxic gas delivery system of the present invention includes unique, non-standard shapes. The parts making up the complete assembly in its various options are the head tent, the hood ring, the neckseal ring, the neck dam, the torso sealing collar, the torso securing collar, and the over-jacket/suspenders. The components of the present invention can be manufactured using a low-cost molding technique which uses an RTV (room temperature vulcanizing) compound. The molds allow manufacture from urethane. Alternatively, standard metal molds can be used.

In some embodiments, for example home users (e.g., family of an autistic child), can be provided access to a central computer system via, for example, the Internet on an anonymous basis to upload patient information and to receive recommendations for dose management (e.g., initial dose and dose adjustments based on an oxygen dose-response model). This exchange of information can be accomplished, for example, through an Internet website. As dose management is based on an oxygen dose-response model/factors, this function can help to individually optimize therapy. It also provides data to be aggregated and used in oxygen dose-response model and process refinement as well as submission to medical regulatory authorities for formal recognition of specific applications. This embodiment may also include an application for both the computer and smart phone that will help the user schedule and record treatments, enter indications of healing, and store results.

In some embodiments, methods of the present may be used to treat or enhance treatment of many other conditions, including, but not limited to other neurological conditions, other normal wound conditions, and other miscellaneous medical conditions. Examples of other neurological conditions include cerebral palsy, traumatic brain injury, stroke, chronic traumatic encephalopathy, amyotrophic lateral sclerosis, chronic pain syndrome, dementia other than Alzheimer's, fibromyalgia, Friedreich's ataxia, Huntington's disease, migraine/cluster headaches, multiple sclerosis, Parkinson's disease, post-traumatic stress disorder, reflex sympathetic dystrophy/complex regional pain syndrome, chronic conditions associated with stroke, and spinal cord injury. Examples of other treatable conditions include developmental disorders such as autism spectrum disorders, Alzheimer's disease, etc. Examples of other treatable normal wound conditions include uncompromised surgical procedures such cosmetic surgery, dental/oral surgery, hair restoration and removal procedures (not including transplants), hair transplant surgery, and physical overuse injury. Examples of other treatable miscellaneous medical conditions include chronic fatigue syndrome, glomerulonephritis, repetitive strain injury, and rheumatoid arthritis, prophylaxis against repetitive strain injuries, delayed onset muscle soreness and inflammatory disorders such as glomerulonephritis and Crohn's disease.

Accordingly, while the present invention has been disclosed in connection with the preferred embodiments thereof, it should be understood that other embodiments may fall within the spirit and scope of the invention, as defined by the following claims.

The invention claimed is:

1. A method comprising:
   applying a hyperoxic therapy delivery system to a patient;
   administering hyperoxic gas to the patient according to an oxygen dose-response model; and
   adjusting the administration of the hyperoxic gas to the patient based upon monitored parameters related to a condition of the patient;
   wherein administering hyperoxic gas includes providing the patient with oxygen or other hyperoxic nitrogen-oxygen gas mixes with a fraction of inspired oxygen ($FiO_2$) of approximately 30% to approximately 100%; and
   wherein the oxygen or other hyperoxic nitrogen-oxygen gas mix is provided at a constant pressure effectively providing a positive end expiratory pressure in a range from approximately 6 cm $H_2O$ to approximately 10 cm $H_2O$.

2. The method of claim 1 wherein applying a hyperoxic delivery system to a patient includes putting a breathing hood assembly on the patient.

3. The method of claim 1 wherein administering hyperoxic gas includes administering hyperoxic gas based upon oxygen dosage.

4. The method of claim 3 wherein administering hyperoxic gas based upon oxygen dosage is performed at approximately one atmosphere of pressure without a whole-body chamber.

5. The method of claim 1 wherein administering hyperoxic gas includes administering hyperoxic gas approximately once per day for up to approximately five days per week.

6. The method of claim 5 wherein administering hyperoxic gas includes administering hyperoxic gas for a duration in the range of approximately 30 minutes to approximately 90 minutes.

7. The method of claim 1 wherein adjusting the administration of the hyperoxic gas includes adjusting the dosage of the oxygen in the hyperoxic gas being administered.

8. The method of claim 7 wherein adjusting the dosage of the oxygen includes adjusting at least one of a fraction of inspired oxygen ($FiO_2$), duration, and frequency of administration of the hyperoxic gas.

9. The method of claim 1 wherein adjusting the administration of the hyperoxic gas includes reducing at least one of $FiO_2$, duration, and frequency of administration of the hyperoxic gas in accordance with the oxygen dose-response model, to maintain effectiveness.

10. The method of claim 1 wherein adjusting the administration of the hyperoxic gas includes assessing monitored parameters.

11. The method of claim 10 wherein the monitored parameters are selected based upon a condition of the patient.

12. The method of claim 11 wherein the condition of the patient is at least one of autism spectrum disorders, cerebral palsy, uncompromised surgical procedures, traumatic brain injury, stroke, and glomerulonephritis.

13. The method of claim 11 wherein the monitored parameters include scores on an evaluation checklist for autism spectrum disorder.

14. The method of claim 11 wherein the monitored parameters include a gross motor function measure (GMFM) for cerebral palsy.

15. The method of claim 11 wherein the monitored parameters include at least one of an immediate post-concussion assessment and cognitive testing (ImPACT) score and a post-traumatic disorder check list (PCL) score for traumatic brain injury.

16. The method of claim 11 wherein the monitored parameters include serum creatinine concentration for glomerulonephritis.

17. The method of claim 11 wherein the condition of the patient is at least one of cosmetic, oral or hair transplant, repetitive strain injury, delayed onset muscle soreness, and chronic traumatic encephalopathy.

18. The method of claim 17 wherein the repetitive strain injury is carpal tunnel syndrome.

19. A method comprising:
    determining an initial oxygen dose-response model for a patient based upon the patient and a condition to be treated;
    applying an initial oxygen dose to the patient in an initial treatment session based upon the initial oxygen dose-response model;
    reassessing the patient's condition periodically;
    adjusting the oxygen dose-response model to reflect the patient's reassessed condition; and
    determining an adjusted oxygen dose based upon the adjusted oxygen dose-response model;
    wherein the oxygen is provided at a constant pressure effectively providing a positive end expiratory pressure in a range from approximately 6 cm $H_2O$ to approximately 10 cm $H_2O$.

20. The method of claim 19 wherein determining an adjusted oxygen dose includes reducing an oxygen dose within an envelope of treatment parameter values of a fraction of inspired oxygen ($FiO_2$) of approximately 30% to approximately 100%, oxygen partial pressure of approximately 0.3 ATM to approximately 1.0 ATM, and absolute pressure of approximately 1 ATA.

21. A system comprising:
    a processor;
    a memory coupled to the processor and operative to store instructions executable on the processor to:
    determine an initial oxygen dose-response model for a patient based upon the patient and a condition to be treated;
    indicate an initial oxygen dose to apply to the patient in an initial treatment session based upon the initial oxygen dose-response model;
    receive data for reassessing the patient's condition periodically;
    adjust the oxygen dose-response model to reflect the patient's reassessed condition; and
    determine an adjusted oxygen dose based upon the adjusted oxygen dose-response model;
    wherein the system is configured to provide oxygen at a constant pressure effectively providing a positive end expiratory pressure in a range from approximately 6 cm $H_2O$ to approximately 10 cm $H_2O$.

\* \* \* \* \*